(12) United States Patent
Kim et al.

(10) Patent No.: US 12,419,974 B2
(45) Date of Patent: Sep. 23, 2025

(54) IMAGING COMPOSITION COMPRISING POROUS SILICON MICRO-PARTICLES

(71) Applicant: UNIVERSITY-INDUSTRY COOPERATION GROUP OF KYUNG HEE UNIVERSITY, Gyeonggi-do (KR)

(72) Inventors: Dokyoung Kim, Seoul (KR); Jaehoon Kim, Seoul (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 722 days.

(21) Appl. No.: 17/365,134

(22) Filed: Jul. 1, 2021

(65) Prior Publication Data
US 2022/0031868 A1    Feb. 3, 2022

(30) Foreign Application Priority Data

May 6, 2020   (KR) .......................... 10-2020-0053855

(51) Int. Cl.
| | |
|---|---|
| A61K 49/00 | (2006.01) |
| A61B 6/00 | (2024.01) |
| A61B 6/03 | (2006.01) |
| B82Y 5/00 | (2011.01) |
| B82Y 30/00 | (2011.01) |
| B82Y 40/00 | (2011.01) |
| C01G 5/00 | (2006.01) |

(52) U.S. Cl.
CPC .......... *A61K 49/0093* (2013.01); *A61B 6/032* (2013.01); *A61B 6/481* (2013.01); *C01G 5/00* (2013.01); *B82Y 5/00* (2013.01); *B82Y 30/00* (2013.01); *B82Y 40/00* (2013.01); *C01P 2004/03* (2013.01)

(58) Field of Classification Search
None
See application file for complete search history.

(56) References Cited

U.S. PATENT DOCUMENTS

| | | | |
|---|---|---|---|
| 6,359,276 B1 * | 3/2002 | Tu .......................... | H10F 39/803 250/332 |
| 2014/0106008 A1 * | 4/2014 | Venter .................... | A01N 59/06 514/738 |
| 2018/0193268 A1 * | 7/2018 | Sailor .................... | A61P 35/00 |
| 2018/0242847 A1 * | 8/2018 | Boppart ............... | A61B 5/7257 |

FOREIGN PATENT DOCUMENTS

| | | | |
|---|---|---|---|
| JP | 05287079 A | * 11/1993 | ............ C08G 77/60 |
| JP | 2005-089369 A | 4/2005 | |
| KR | 10-2008-0067333 A | 7/2008 | |
| KR | 10-2010-0071258 A | 6/2010 | |

OTHER PUBLICATIONS

Liu (Silica/ultrasmall Ag composite microspheres: facile synthesis, characterization and antibacterial and catalytic performance, Dec. 17, 2013, CrystEngComm, 16:2365) (Year: 2013).*
Gu (Synthesis and antibacterial property of hollow SiO2/Ag nanocomposite spheres, Apr. 13, 2011, Journal of Colloid and Interface Science, 359:327-333) (Year: 2011).*
Selim (Silicone/Ag@SiO2 core-shell nanocomposite as a self-cleaning antifouling coating material, Mar. 8, 2018, RSC Advances, 8: 9910) (Year: 2018).*
Gao (Plasmonic photothermic directed broadband sunlight harnessing for seawater catalysis and desalination, Jun. 6, 2016, Energy and Environmental Science) (Year: 2016).*
[Oxford English Dictionary, "Embed"] (Year: 2024).*
[Oxford English Dictionary, "Bond"] (Year: 2024).*
Kim (Composite Porous Silicon-Silver Nanoparticles as Theranostic Antibacterial Agents, Oct. 18, 2016, ACS Applied Materials and Interfaces, 8:30449-30457). (Year: 2016).*
Office Action from corresponding Korean Patent Application No. 10-2020-0053855, dated Jun. 27, 2021.
Taeho Kim et al., "Composite Porous Silicon-Silver Nanoparticles as Theranostic Antibacterial Agents", ACS Appl. Mater. Interfaces. 2016, vol. 8, No. 44, pp. 30449-30457.

* cited by examiner

*Primary Examiner* — Michael G. Hartley
*Assistant Examiner* — Kaila A Craig
(74) *Attorney, Agent, or Firm* — Harness, Dickey & Pierce, P.L.C.

(57) ABSTRACT

The present disclosure describes an imaging composition including porous silicon microparticles, and more particularly, to a biological tissue imaging composition including a composite in which oxidized porous silicon microparticles and silver nanoparticles are combined. Since a biological tissue imaging agent of the present invention, which includes a composite of oxidized porous silicon microparticles and silver nanoparticles, continuously provides an image signal without spreading in the body as compared to conventional imaging agents, it is possible to increase surgical stability by accurately identifying target tissues in vivo in an affected area.

6 Claims, 22 Drawing Sheets

IMAGING COMPOSITION COMPRISING POROUS SILICON MICRO-PARTICLES

CROSS-REFERENCE TO RELATED APPLICATION

This application claims priority to and the benefit of Korean Patent Application No. 2020-0053855, filed on May 6, 2020, the disclosure of which is incorporated herein by reference in its entirety.

FIELD

The present disclosure describes an imaging composition including porous silicon microparticles, and more particularly, to a biological tissue imaging composition including a composite in which oxidized porous silicon microparticles and silver nanoparticles are combined.

BACKGROUND

An imaging composition is a material used for improving the visualization, particularly contrast, of the inside of the body in an image generated using any one of various imaging techniques. These techniques or modalities include, but are not limited to, X-rays, computed tomography (CT) imaging, magnetic resonance imaging (MRI), scintigraphy, fluorescence, and ultrasound. The imaging composition may be used for accurately locating a body or a body part, including an organ or tissue, in an accurate position or field of view for imaging or treatment.

Meanwhile, lung cancer is a malignant lung tumor characterized by uncontrolled cell growth in lung tissue, and CT imaging can be used to determine whether a patient has developed lung cancer. Solitary pulmonary nodules (SPNs) and subfebrile nodules (SNs) observed in lung cancer patients exhibit heterogeneous characteristics and malignant potential. In the early stages of lung cancer, surgery for removing the SPNs and SNs from the lungs is essential.

In early stage lung tumor resection, video-assisted thoracoscopic surgery (VATS) can reduce the burden on the patient's body and increase a survival rate as compared to a thoracotomy (Kaseda. S. et al., Ann. Thorac. Surg. 2000, 70, 1644; Whitson. B. A. et al., Ann. Thorac. Surg. 2008, 86, 2008).

Recently, VATS using CT imaging has become a standard method in tissue sample biopsy and lung cancer surgery due to its minimal invasiveness and high stability. However, it is difficult to accurately locate SPNs and SNs during VATS, due to two main reasons: (i) SPNs and SNs are very small and located far from the pleura, and (ii) due to lung collapse, a distorted field image is not consistent with a previously determined CT image. Therefore, the accurate labeling of small and deeply located SPNs and SNs before performing VATS is essential to minimize image distortion and increase the success rate of VATS surgery.

Recently, various lung localization targeting technologies (LLTTs), metal materials (e.g., hookwires, microcoils), organic dyes (e.g., methylene blue (MB), indigo carmine (IC)), radioactive tracers (e.g., TCm), and contrast agents (e.g., barium sulfate, Lipiodol) have been introduced. Among these, Lipiodol, which is a CT-based targeting agent, is most widely used in VATS because it causes less discomfort to the patient during surgery, is simple and easy to use, has a mild inflammatory response, involves no radiation exposure, and can provide information at the depth of the lesion.

Lipiodol is a radiopaque contrast agent formed of poppyseed oil and iodine. Despite the many advantages of VATS with respect to SPNs and SNs, Lipiodol has serious drawbacks such as the risk of leakage in the pleural cavity and embolism due to low water solubility. (Y. D. Kim, Y. J. Jeong, I. Hoseok, J. S. Cho, J. W. Lee, H. J. Kim, S. H. Lee and D. H. Kim, Actaradiol., 2011, 52, 64-69.) In addition, when labeling is applied near the trachea, a side effect that Lipiodol spreads to the entire lung or to the bronchi may occur due to the pressure caused by breathing, and because Lipiodol spreads rapidly after injection, there is a risk of removing a larger area than the tumor area to be removed. Therefore, it is necessary to develop a new imaging material that does not spread to other organs after being injected into a specific site.

SUMMARY

The present inventors have developed a novel composite in which silver nanoparticles are attached to oxidized porous silicon microparticles. As a result of making research efforts to develop a contrast agent for imaging that does not show a toxic reaction when injected into a tissue in vivo, provides a strong image signal, and does not spread around an injection site, the present inventors developed a composite (pSi-Ag-MPs) in which oxidized porous silicon microparticles and silver nanoparticles are combined, and confirmed that the composite does not spread to organs other than a specific labeled site after in vivo injection, and thereby completed the present disclosure.

Therefore, the present disclosure is directed to providing a biological tissue imaging composition including a composite in which oxidized porous silicon microparticles and silver nanoparticles are combined.

In addition, the present disclosure is directed to providing a biological tissue imaging agent in which the composite is diluted in a mixture of a glycerol solution and water.

In addition, the present disclosure is directed to providing a method of preparing a biological tissue imaging composition, which includes: a) oxidizing porous silicon microparticles; and b) attaching silver nanoparticles to the silicon microparticles.

In addition, the present disclosure is directed to providing a method of manufacturing a biological tissue imaging agent, which includes diluting the above biological tissue imaging composition in a mixture of a glycerol solution and water.

However, the technical objectives of the present disclosure are not limited to the above-described objectives, and other unmentioned objectives will be clearly understood by those of ordinary skill in the art from the following description.

One aspect of the present disclosure provides a biological tissue imaging composition including a composite in which oxidized porous silicon microparticles and silver nanoparticles are combined.

Another aspect of the present disclosure provides a biological tissue imaging agent manufactured by diluting a composite in which oxidized porous silicon microparticles and silver nanoparticles are combined, in a mixture of a glycerol solution and water.

Still another aspect of the present disclosure provides a method of preparing a biological tissue imaging composition, which includes: a) oxidizing porous silicon microparticles; and b) attaching silver nanoparticles to the silicon microparticles.

Yet another aspect of the present disclosure provides a method of manufacturing a biological tissue imaging agent, which includes diluting the above biological tissue imaging composition in a mixture of a glycerol solution and water.

BRIEF DESCRIPTION OF THE DRAWINGS

The above and other objectives, features, and advantages of the present disclosure will become more apparent to those of ordinary skill in the art by describing exemplary embodiments thereof in detail with reference to the accompanying drawings, in which.

DETAILED DESCRIPTION

Figure 1:
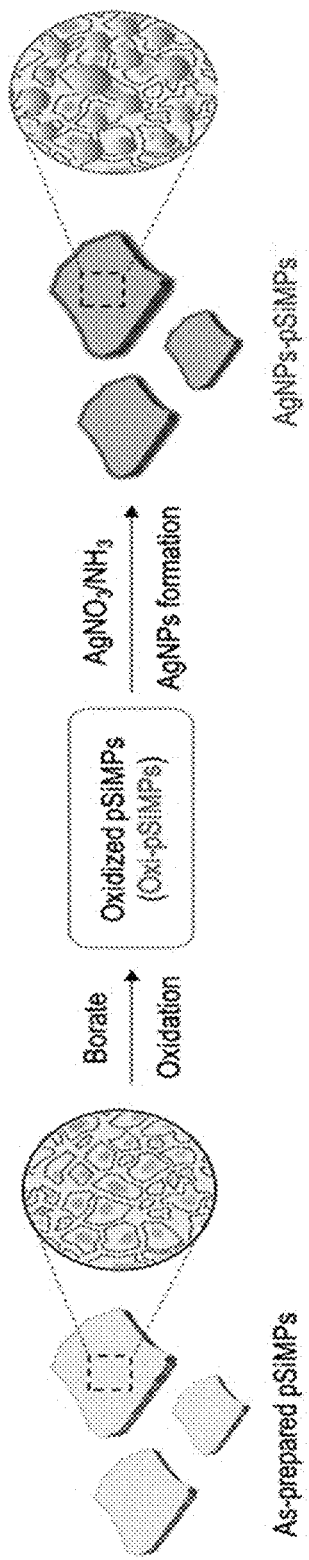
FIG. 1 is a schematic diagram of a method of manufacturing a composite of oxidized porous silicon microparticles and silver nanoparticles.

Hereinafter, the present disclosure will be described in detail.

One aspect of the present disclosure provides a biological tissue imaging composition including a composite in which oxidized porous silicon microparticles and silver nanoparticles are combined.

According to one specific embodiment of the present disclosure, the size of the porous silicon microparticles may be 1 to 10 μm, preferably 3 to 7 μm, and more preferably 5 μm.

According to another specific embodiment of the present disclosure, the composite may include elemental silicon, elemental oxygen, and elemental silver in a weight ratio of 100:100 to 120:15 to 30, preferably in a weight ratio of 100:105 to 115:20 to 25, and more preferably in a weight ratio of 100:113:24.

Another aspect of the present disclosure provides a biological tissue imaging agent prepared by diluting the above-described composite in a mixture of a glycerol solution and water.

According to one specific embodiment of the present disclosure, the mixture may be a solution in which a glycerol solution and water are mixed in a ratio of 2 to 4:1, preferably a solution in which a glycerol solution and water are mixed in a ratio of 2.5 to 3.5:1, and more preferably a solution in which a glycerol solution and water are mixed in a ratio of 3:1.

According to another specific embodiment of the present disclosure, the biological tissue imaging may be performed by MRI, X-ray imaging, scintigraphy, fluorescence, ultrasound, or CT imaging and preferably CT imaging.

According to still another specific embodiment of the present disclosure, the biological tissue may include lung, liver, heart, kidney, and stomach tissues, and is preferably the lung tissue.

Still another aspect of the present disclosure provides a method of preparing a biological tissue imaging composition, which includes: a) oxidizing porous silicon microparticles; and b) attaching silver nanoparticles to the silicon microparticles.

According to one specific embodiment of the present disclosure, the porous silicon microparticles may include an oxidized silicon (Si) framework ($SiO_2$).

According to another specific embodiment of the present disclosure, the attachment of the silver nanoparticles may be achieved using an aqueous silver bis-amine solution ([Ag(NH$_3$)$_2$]$^+$).

According to still another specific embodiment of the present disclosure, the oxidization may be achieved using a borate.

Yet another aspect of the present disclosure provides a method of manufacturing a biological tissue imaging agent, which includes diluting the above-described biological tissue imaging composition in a mixture of a glycerol solution and water.

According to one specific embodiment of the present disclosure, the mixture may be a solution in which a glycerol solution and water are mixed in a ratio of 2 to 4:1, preferably a solution in which a glycerol solution and water are mixed in a ratio of 2.5 to 3.5:1, and more preferably a solution in which a glycerol solution and water are mixed in a ratio of 3:1.

As used herein, the term "porous silicon microparticle" refers to a particle having a particle size of 1 to 10 μm and a pore size of 5 to 100 nm and including elemental silicon, elemental carbon, and elemental oxygen as constituent components. The porous silicone microparticles are non-toxic and decomposable in vivo, are capable of loading a large amount of material due to having high porosity, and are a hard inorganic material and thus remain in place rather than moving after being injected in vivo.

As used herein, the term "nanoparticle" refers to a material having a basic unit size of 1 to 100 nm, and the nanoparticles exhibit various properties depending on the size of each unit, composition, shape, mode of combination, and the surface morphology of each material. Nanotechnology makes it possible to target tumors, effectively deliver drugs, genes, and contrast agents to diseased sites, control drug release by external stimuli, and even image drug responses. When various drugs and contrast agents are loaded onto nanoparticles through various chemical methods, it is possible to construct a multifunctional nano-drug delivery system labeled with cancer cell-specific target materials, which can be utilized for cancer targeting, treatment, and imaging.

As used herein, the term "biological tissue imaging composition" is a material used for improving the visualization, particularly contrast, of the body in an image generated using any one of various imaging techniques. The biological tissue imaging composition can be used for accurately locating a body or a body part, including an organ or tissue, in an accurate position or field of view for imaging or treatment.

As used herein, the term "imaging agent" refers to a material which has been developed to be visible in specific modalities by virtue of its biophysical properties and thus is capable of providing signals to anatomical structures. The imaging agent may be administered through a needle, catheter, nebulizer, or the like, and may be in the form of a liquid, solid, or aerosol. In addition, the imaging agent can be used for laparotomy or VATS.

The present inventors have developed a biological tissue imaging composition including a composite (pSi-Ag-MPs) of oxidized porous silicon microparticles and silver nanoparticles and confirmed, through specific exemplary embodiments, that an imaging agent including the above composition generates a sufficient image signal in vivo to enable imaging of a target site and does not spread to other organs.

In one exemplary embodiment of the present disclosure, as a result of measuring the image signal of a composite of the present disclosure in vitro, it was confirmed that the composite exhibited sufficient image signal intensity as an in vivo imaging material. From the results of the exemplary embodiment, it can be seen that a biological tissue imaging composition including the composite can be effectively used for VATS and can be usefully utilized for the imaging of miscellaneous tissues (See Example 5-1).

In another exemplary embodiment of the present disclosure, it was found that when glycerol is included at 70 to 80% in the mixture, an optimal balance can be achieved between the pressure of the lungs and the injection force of a syringe (See Example 5-2).

In still another exemplary embodiment of the present disclosure, as a result of injecting an imaging agent of the present disclosure into the lungs of a rabbit and performing in vivo imaging, it was found that only the tissues (lungs) injected with the imaging agent of the present disclosure showed local reactivity (See Example 6).

In yet another exemplary embodiment of the present disclosure, as a result of injecting an imaging agent of the present disclosure or an lipopolysaccharide (LPS) into the lung tissue, it was found that when the imaging agent was injected, toxicity was lower than when the LPS was injected (See Example 7).

Hereinafter, exemplary embodiments are provided to help the understanding of the present disclosure. However, the following exemplary embodiments are provided only to facilitate the understanding of the present disclosure, and the content of the present disclosure is not limited by the exemplary embodiments.

EXAMPLES

Example 1. Experimental Preparation 1-1. Materials

Commercial reagents used in this study were purchased from Sigma-Aldrich (US), Alfa Aesar (US), Tokyo Chemical Industry (TCI; Japan), and Samchun Chemicals (Rep. of Korea). Sodium tetraborate decahydrate (CAS No. 1303-96-4) and silver nitrate (CAS No. 7761-88-8) were purchased from Alfa Aesar (US). An ammonia solution (28% in $H_2O$, CAS No. 1336-21-6) was purchased from TCI (Japan). Ethanol (product No. E0223) was purchased from Samchun Chemicals. Glycerol (CAS No. 56-81-5) was purchased from Alfa Aesar (US). Pre-prepared pSiMPs was provided by TruTag Technologies (Kapolei, Hawaii, US) (pSiMP product No.: TruTagmicrotags (batches 200-3292, 200-3293, 200-3294)).

1-2. Used Instruments

Particle morphology was examined by SEM (SU8220, Hitachi, Japan). Surface components of particles were analyzed by EDX (E-max Evolution EX-370 (Analyzer), X-Max 50 (Detector), Horiba, Japan). The surface function of particles was analyzed by attenuated total reflection (ATR)-FTIR (Nicolet iS5, ASB1817871, Thermo Fisher Scientific, Waltham, MA, USA). The crystallinity of particles was measured by XRD (X'-Pert-PRO MPD, Panalytical. B.V., Warsaw, Poland) and atomic force microscopy (AFM)-Raman spectroscopy (NT-MDT, Russia). XRD spectra were collected at room temperature under the conditions of a scan speed of 0.1 seconds/step and a step size of 0.017° at 2ϕ, and a 2ϕ range of 5 to 80°. Raman analysis was performed using a 437 nm (100 mW) laser wavelength band. Gas adsorption isotherms were measured using a BEL Belsorp mini II gas adsorption instrument (Mictrotrac BEL, Japan) with a gas pressure of up to 1 atm. The isotherms were measured at 77 K using pure $N_2$ (99.999%). The measurement was performed using a gas adsorption method (BET), and before a nitrogen adsorption experiment, particles were degassed at 120° C. under vacuum overnight. The SEM, XRD, Raman, BET, and EDS analyses were performed at the Korea Basic Science Institute (Korea University, Seoul, Rep. of Korea). An incubator (Orbital Shaker-Incubator, RC-41W-0001, Hangzhou Ruicheng Ins., China) was used for the preparation of a composite of the present disclosure. An ultrasonic cleaner (97043-960, VWR, US) and a centrifuge (Eppendorf Centrifuge model 5418, 5418FQ924939, Eppendorf AG, US) were used in a washing step in the preparation of a composite of the present disclosure.

1-3. Preparation of Oxidized Porous Microparticles

Oxidized porous microparticles were prepared using a borate. After dispersing porous microparticles (10 mg) in a glass vial (20 mL size), an aqueous borate solution (borax, 40 mM, 0.5 mL), ethanol (1.0 mL), and distilled water (0.5 mL) were added at room temperature (25° C.) while magnetically stirring (450 rpm). After stirring for six hours, the resulting particles were collected by centrifugation (14,000 rpm, 15 min) and then washed three times with distilled water.

1-4. Preparation of Composite (Psi-Ag-MPs) of Present Invention

For the preparation of a composite of the present disclosure, an aqueous silver bis-amine solution $[Ag(NH_3)_2)]^+$ was used as a silver precursor. The aqueous silver bis-amine solution was prepared in a glass vial (20 mL) by adding a mixture of an aqueous ammonia solution (1 M, 200 μL) and distilled water (2.8 mL) to a silver nitrate solution ($AgNO_3$, 1 M, 0.75 mL). Subsequently, after dispersing the oxidized porous silicon microparticles (50 mg) previously treated with the aqueous borate solution in 25 mL of distilled water, a 1.5 mL aliquot of the aqueous silver bis-amine solution $[Ag(NH_3)_2]^+$ was added. Subsequently, after inputting a tube containing the porous silicon microparticles into an incubator, stirring was performed for three hours at room temperature (25° C.) while shaking (300 rpm). After stirring, particles were collected by centrifugation (1,400 rpm, 3 min) and then washed three times with distilled water.

Example 2. Imaging Methods 2-1. Animals

New Zealand male white rabbits (3 to 3.5 kg) were used for micro-CT chest imaging (Approval No.: 2017-0338 (Approved by Yonsei University Health System Institutional Animal Care and Use Committee (IACUC), Rep. of Korea)).

2-2. Protocols

New Zealand male white rabbits (n=6, weight: 3.0 to 3.5 kg) were locally anesthetized by intramuscular injection of Zoletil (30 mg/kg) and xylazine (5 mg/kg) and imaged along up and down directions in the supine position. First, an area where a needle hole will be formed was selected and sterilized. According to a CT-fluorescence method, 0.2 cc of a composite of the present disclosure was directly injected into the lungs of the rabbits through a needle of a sterile 1 cc syringe. After injecting the composite of the present disclosure, the injection needle was removed, and CT scans were performed at 0, 15, 30, and 60 minutes to evaluate the accumulation degree and CT intensity of the injected composite.

2-3. Setup

Chest CT scans were performed using a 64-slice multiple detector human CT scanner (Discovery CT750 HD; GE Healthcare) to which a CT-fluorescence method is applied. Scan parameters are as follows: Detector collimation=64× 0.625 mm; gantry rotation time=0.5 seconds; tube voltage=120 kV; tube current=200 mA; and pitch=0.984:1. All images were reconstructed using a 0.625 mm slice thickness.

2-4. Immunotoxicity Assay Animals

C57BL/6J mice without specific pathogens were provided by the animal facility of the Seoul National University College of Medicine. Six- to eight-week-old male mice weighing 20 to 25 g were used for the experiment. The animal protocol for the experiment was reviewed and approved by the Seoul National University Ethics Committee.

2-5. Treatment with Composite of Present Invention

A composite of the present disclosure (mice=142 μg/25 g; rabbits=20 mg/3.5 kg) and an LPS (Sigma-Aldrich Co. LLC., St. Louis, MO; extracted from *E. coli* in an amount of 10 mg/kg) were administered to mice by intraperitoneal injection. An equal amount of 75% glycerol was injected into a control group. For cytokine measurement, blood was collected two hours after the injection. 24 hours after treatment, the activities of ALT and AST plasma enzymes were measured using a kit suitable for the purpose (Sigma-Aldrich Co. LLC.), and liver damage was quantified according to the manufacturer's instructions.

2-6. Cytokine Measurement

Blood was collected from the intestinal pleura using heparinized capillary tubes, and plasma was obtained by centrifugation. The amount of cytokines in the plasma was measured by enzyme-linked immunosorbent assay (ELISA). A TNF-α ELISA kit was purchased from BioLegend, Inc. (San Diego, CA, US). The ELISA was performed according to the manufacturer's instructions.

2-7. Isolation of Splenocytes

After euthanizing the mice, the spleen was aseptically removed and added along with 100 U/ml of penicillin and 100 μg/ml of streptomycin to a wash medium containing cold RPMI640 (WELGENE, Daegu, Rep. of Korea). The spleen was homogenized, passed through a 70-μm cell strainer, and centrifuged at 600 g for 10 minutes. The resulting pellet was collected and resuspended in a red blood cell (RBC) lysis buffer. Cells were washed in a wash medium and then counted.

2-8. Flow Cytometry

Splenocytes were resuspended in a cold fluorescence-activated cell sorting (FACS) buffer containing 0.5% bovine serum albumin (BSA) at 8 and 24 hours after injection, and then were treated with the TruStainFcX antibody (BioLegend, Inc., San Diego, CA, US) at room temperature (25° C.) for 10 minutes and thus formed into blocks. Subsequently, the cells were stained with anti-CD25/CD69/CD80/CD86 (BD Biosciences, San Jose, MN, US) on ice for 30 minutes. The cells were washed with a cold FACS buffer and then analyzed with a FACSCalibur (BD Biosciences, San Jose, MN, US). For data analysis, FlowJo Software (Tree Star, Inc., Ashland, OR, US) was used.

2-9. Liver and Kidney Damage Tests

After anesthetizing mice with Zoletil (25 mg/kg) and Rompun (10 mg/kg), the portal vein was equilibrated, and the liver was perfused with sterile phosphate-buffered saline (PBS; pH 7.4). The liver and kidney tissues were removed and fixed in 4% p-formaldehyde for immunohistochemistry, and fixed in paraffin at 8 and 24 hours after injection. For histological examination, sections were stained with hematoxylin and eosin (H&E).

2-10. Statistical Analysis

Data is presented as mean±standard deviations (SDs). For the comparison of two groups [control vs. pSi-Ag-MPs or pSi-Ag-MPs vs. LPS], an unpaired two-tailed t-test was performed. A p-value of less than 0.05 was considered statistically significant. Statistical tests were performed using GraphPadInStat version 5.01 (GraphPad Software, La Jolla, CA, US).

Example 3. Synthesis of Composite

Figure 2:
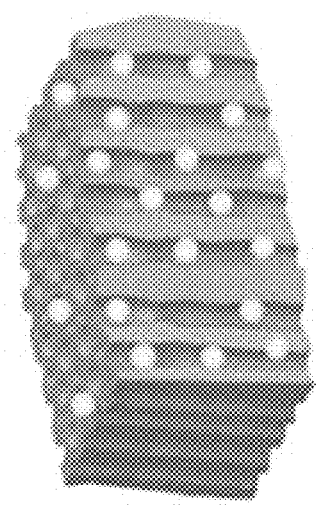
FIG. 2 is a schematic diagram of a composite of oxidized porous silicon microparticles and silver nanoparticles.
Figure 2:
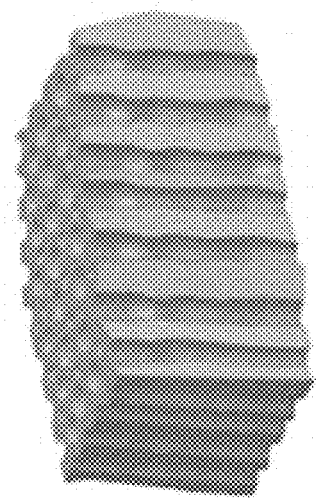

An experiment for synthesizing a composite of oxidized porous silicon microparticles and silver nanoparticles according to the present disclosure was performed. A method of synthesizing a composite of the present disclosure is illustrated in FIG. 1, and a final composite synthesized thereby is illustrated in FIG. 2.

First, porous silicon microparticles were prepared using a constant anodization current of a heavy boron-doped p-type polished ((100) plane) single crystal silicon wafer in an ethanolic hydrofluoric acid (HF) electrolyte. Then, a 10 mg aliquot of 50 mg of the porous silicon microparticles (particle size: 5 μm) was added to each of 20 mL vials, and 0.5 mL of an aqueous borate solution (sodium tetraborate decahydrate, 381 mg, 40 mM, borate) was added to each of the vials. Subsequently, 1 mL of a 100% ethanol solution and 0.5 mL of distilled water were added.

Subsequently, stirring was performed at room temperature (25° C.) for six hours. Then, oxidized porous silicon microparticles were settled using a centrifuge (14,000 rpm, 15 min) and washed three times with distilled water. The oxidized porous silicon microparticles (named Oxi-pSiMPs) have an oxidized Si structure ($SiO_2$). This oxidation step is essential for improving the hydrophilicity of the microparticles and inducing the formation of silver ion nanoparticles on the surface.

Subsequently, an aqueous silver bis-amine solution ($[Ag(NH_3)_2]^+$) was prepared by mixing a 1 M aqueous ammonia solution (200 μL), 2.8 mL of distilled water, and 0.75 mL of an aqueous silver nitrate solution (1 M). After adding 25 mg of the porous silicon microparticles treated with the aqueous borate solution to each of 50 mL tubes, 25 mL of distilled water was added to disperse the microparticles, and then 1.5 mL of an aqueous silver bis-amine solution was added. Subsequently, after stirring for three hours, the resultant was washed three times with distilled water using a centrifuge (14,000 rpm, 3 min). The solvent was removed from the product (pSi-Ag-MPs) using a freeze dryer, and finally, a composite of the present disclosure was obtained.

The obtained material was named a porous silicon microparticle-silver nanoparticle composite (pSi-Ag-MPs).

Figure 3:
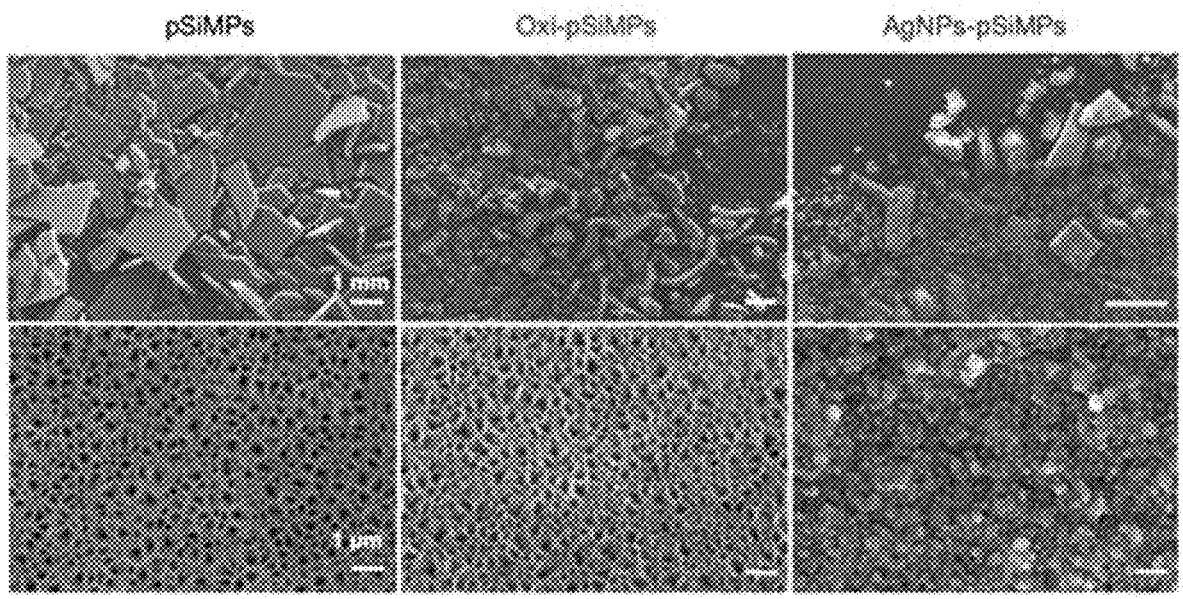
FIG. 3 shows the scanning electron microscopic (SEM) imaging results of porous silicon microparticles, oxidized porous silicon microparticles, and a composite of the present disclosure.

Example 4. Characterization of Composite (pSi-Ag-MPs) of Present Invention 4-1. Characterization of Porous Structure of Composite of Present Invention For the morphological or chemical characterization of the composite (pSi-Ag-MPs) of the present disclosure, the SEM image analysis of porous silicon microparticles, oxidized porous silicon microparticles, and the composite of the present disclosure was performed. That is, SEM images as shown in FIG. 3 were obtained. As shown in FIG. 3, planar porous silicon microparticles having a particle size of 1 to 3 mm were mainly observed, and in the plan view of the samples, open porous structures with a pore size of 5 to 100 nm were observed (FIG. 3, left).

According to the SEM images of the oxidized porous silicon microparticles, it can be seen that, although the particle size was reduced due to oxidization and crushing during washing, the porous structure was maintained (FIG. 3, middle).

It can be seen that, although the porous structure of the composite of the present disclosure was destroyed due to the bonding/loading of silver nanoparticles into pores and the oxidation of porous silicon microparticles during reaction, the particle size remained the same (FIG. 3, right).

4-2. Characterization of Molecular Structure of Composite of Present Invention

Figure 4:
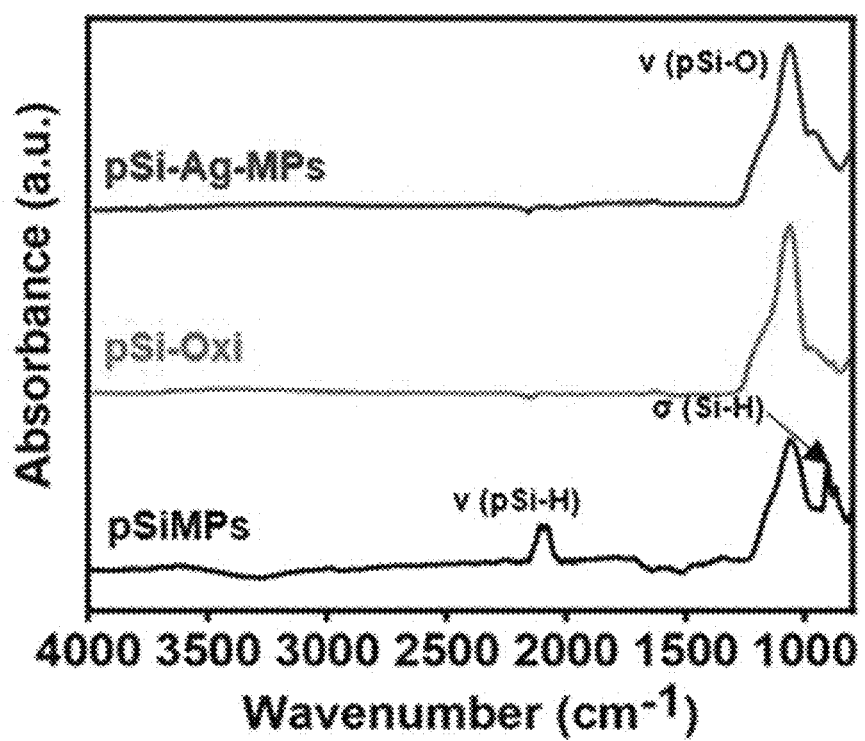
FIG. 4 shows Fourier transform infrared (FTIR) measurement results according to composite synthesis steps.

ATR-FTIR was performed to characterize the molecular structure of the composite of the present disclosure. Referring to FIG. 4, it can be seen that the porous silicon microparticles, which are a synthesis precursor material and had not yet been oxidized, had a structure in which hydrogen (H) was bonded to Si, whereas the oxidized porous silicon microparticles and the composite (pSi-Ag-MPs) of the present disclosure mainly had a structure in which oxygen (O) was bonded to Si.

Figure 5:
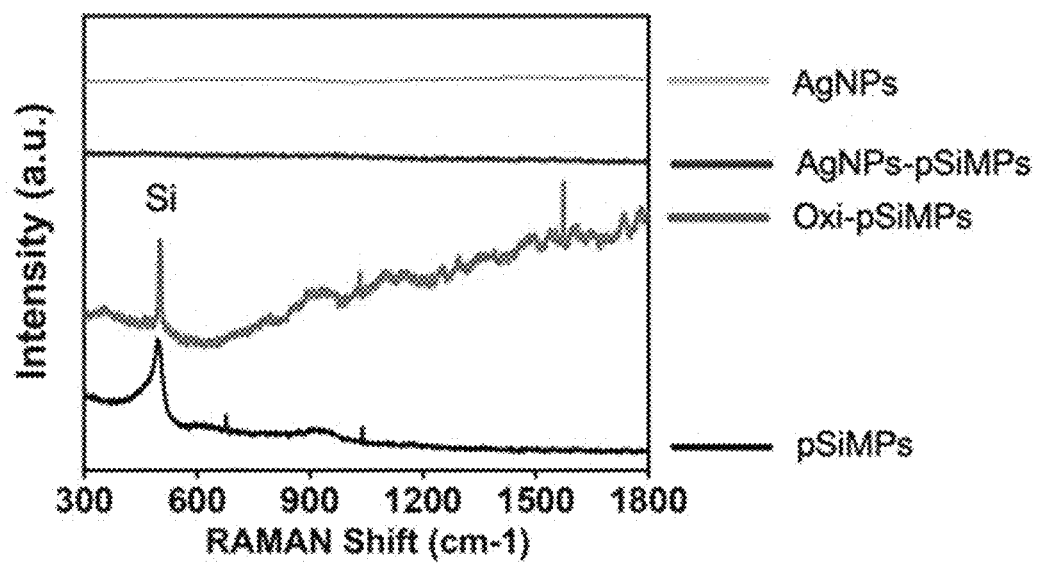
FIG. 5 shows Raman spectroscopy ("RAMAN") measurement results according to composite synthesis steps.

4-3. Confirmation of Attachment of Silver Nanoparticles in Composite of Present Invention The Raman analysis of the composite of the present disclosure was performed to confirm the attachment of silver nanoparticles to the porous silicon microparticles. As a control, porous silicon microparticles and oxidized porous silicon microparticles were used, and the Raman analysis results thereof showed the crystallinity of the Si framework (Si lattice mode: 495 $cm^{-1}$). As shown in FIG. 5, mainly elemental Si was observed in the porous silicon microparticles, which are a synthesis precursor material, and the oxidized porous silicon microparticles mainly consisted of Si and O. On the other hand, in the case of the composite of the present disclosure in which silver ion particles were attached, considering the fact that the signal intensity of silver nanoparticles is very large and a saturated signal is observed, it can be confirmed that the silver nanoparticles are attached to the porous silicon microparticles.

Figure 6:
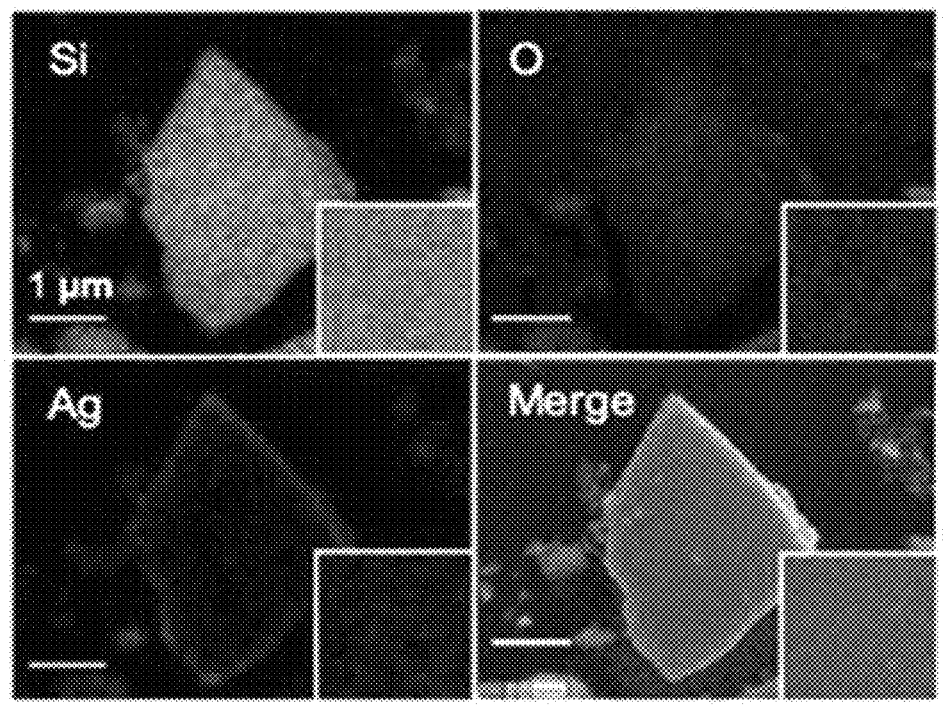
FIG. 6 shows the energy-dispersive X-ray spectroscopy (EDX) elemental analysis and imaging results of the silicon, oxygen, and silver of a composite of the present disclosure.
Figure 7:
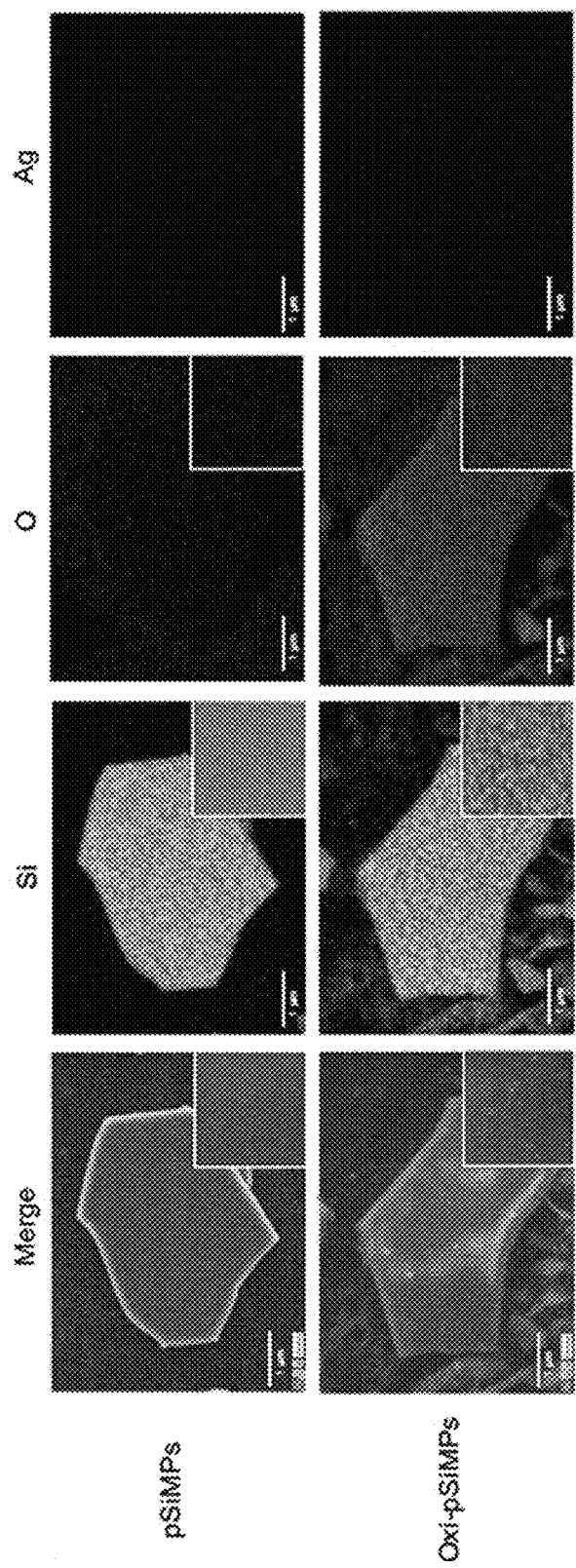
FIG. 7 shows the EDX elemental analysis and imaging results of the silicon, oxygen, and silver of porous silicon microparticles and oxidized porous silicon microparticles.

4-4. Confirmation of Uniform Attachment of Silver Nanoparticles to Surface of Composite of Present Invention EDX was performed on the composite of the present disclosure to confirm the uniform attachment of silver nanoparticles to a surface of porous silicon microparticles. EDX was performed at each composite synthesis step to evaluate a change in the surface of the porous silicon microparticles, and the results are shown in FIGS. 6 to 8.

Figure 8:
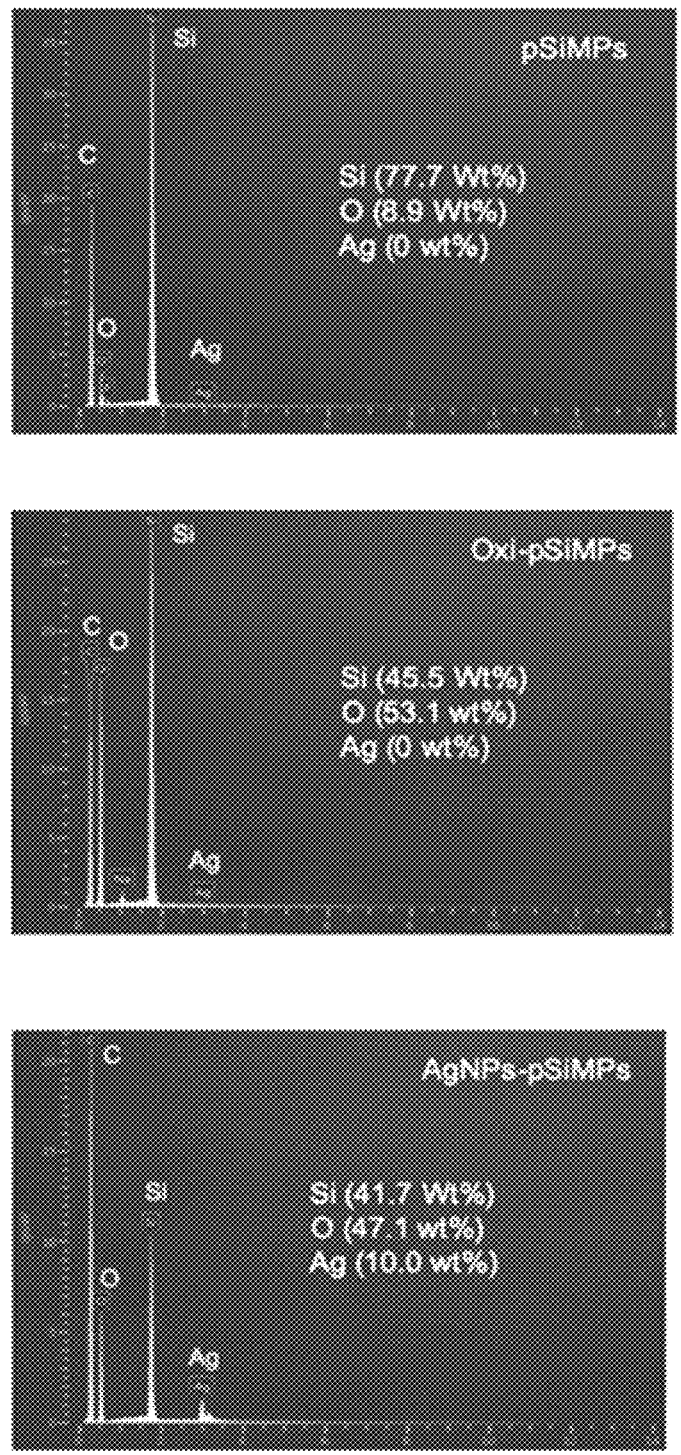
FIG. 8 shows the EDX measurement results of porous silicon microparticles, oxidized porous silicon microparticles, and a composite of the present disclosure.

As determined by EDX, Si (77.7%) was the most important element in the synthesis precursor material, porous silicon microparticles (FIG. 8, left), and after oxidation, more O (53.1%) was present on the surface than Si (45.5%) (FIG. 8, middle), and in the case of the composite of the present disclosure in which silver ion particles were attached, approximately 10.0% silver nanoparticles were attached to the surface (FIG. 8, right).

From the above experimental results, it was confirmed that the silver nanoparticles were uniformly attached to the surface of the composite of the present disclosure.

4-5. Characterization of Lattice Structure of Composite of Present Invention

Figure 9:
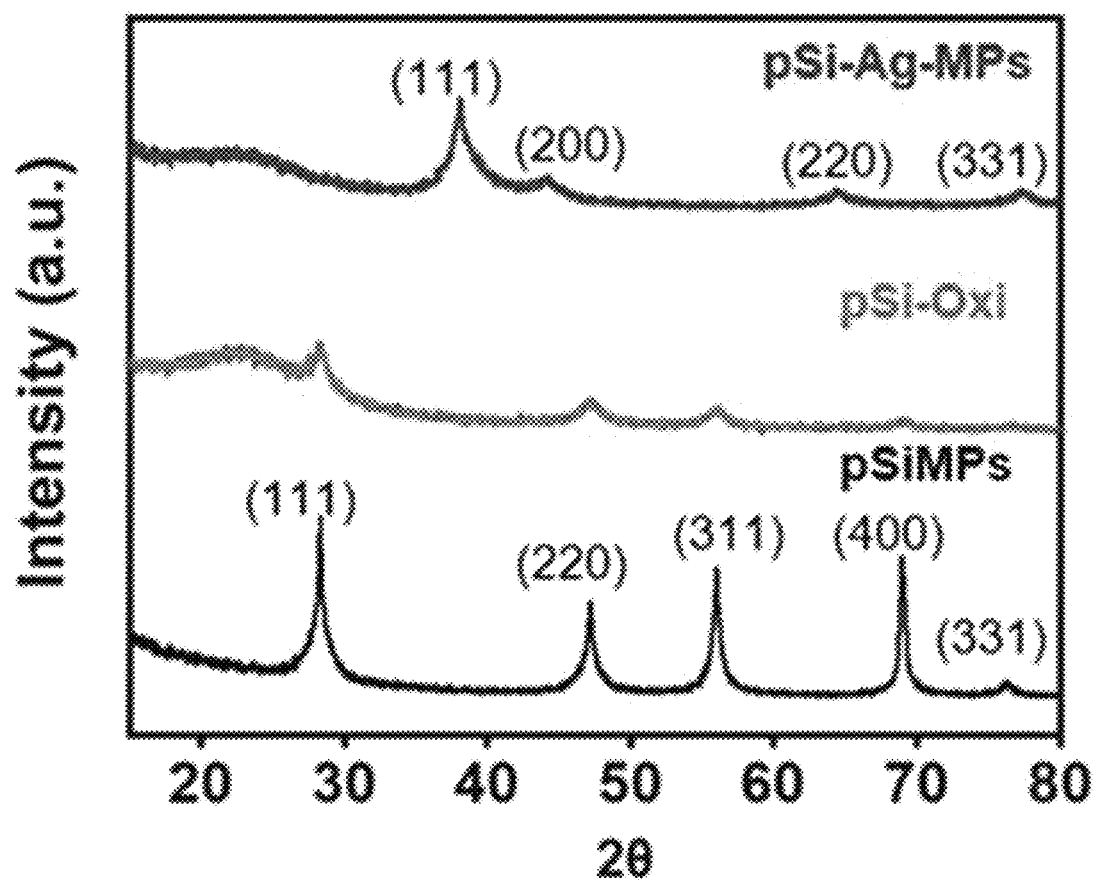
FIG. 9 shows X-ray diffraction (XRD) results according to composite synthesis steps.

XRD was performed on porous silicon microparticles, oxidized porous silicon microparticles, and the composite of the present disclosure to evaluate a change in the lattice structure of the composite of the present disclosure, and the results are shown in FIG. 9.

As a result, it can be seen that the synthesis precursor material, porous silicon microparticles, and the oxidized porous silicon microparticles had the same lattice structures, but the composite of the present disclosure showed a silver nanoparticle lattice structure due to the silver nanoparticles attached to the surface. Therefore, it was confirmed that the silver nanoparticles were attached to the composite.

4-6. Evaluation of Surface Area and Pore Size of Composite of Present Invention

Figure 10:
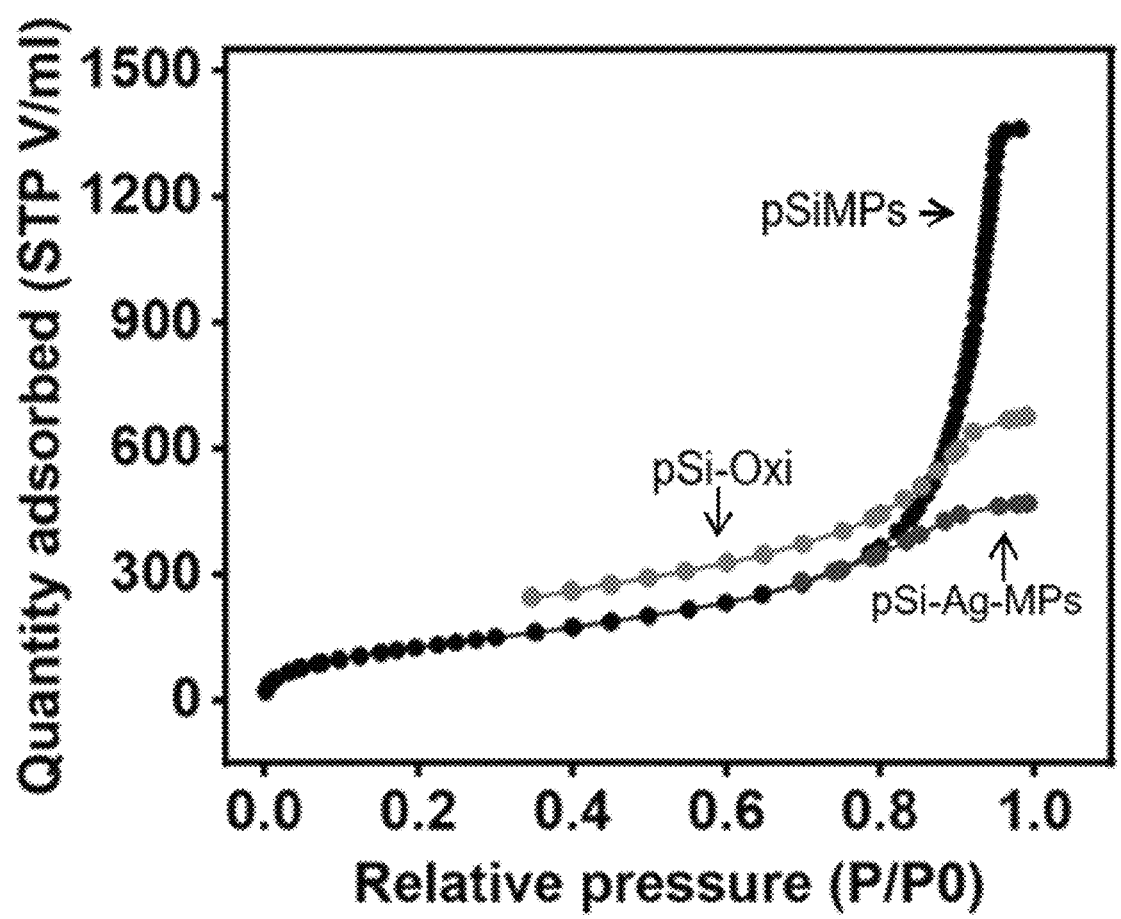
FIG. 10 shows nitrogen adsorption-desorption (Brunauer-Emmett-Teller (BET)) measurement results according to composite synthesis steps.

The composite of the present disclosure was morphologically characterized through nitrogen adsorption-desorption for each material of the synthesis steps, and the results are shown in FIG. 10. Referring to FIG. 10, it can be seen that, as shown in Table 1, as the synthesis precursor material, porous silicon microparticles, were oxidized, pores on the surface were lost, and thus a pore size changed.

TABLE 1

|  | BET surface area $(m^2 \cdot g^{-1})$ | BJH pore volume $(cm^3 \cdot g^{-1})$ | BJH pore size (nm) |
| --- | --- | --- | --- |
| pSiMPs | 477.47 | 2.1407 | 9.23 |
| Oxi-pSiMPs | 725.85 | 0.9587 | 1.21 |
| pSi-Ag-MPs | 471.26 | 0.6998 | 1.85 |

According to the pore size and volume data obtained using the Barrett-Joyner-Halenda (BJH) method, a smaller pore volume and size were observed after oxidation. Whereas the porous silicon microparticles had a pore size of 9.23 nm, the composite of the present disclosure had a significantly reduced pore size of 1.85 nm. Therefore, it can be seen that the composite of the present disclosure had a reduced surface area and pore size as compared to the precursor.

Figure 11:
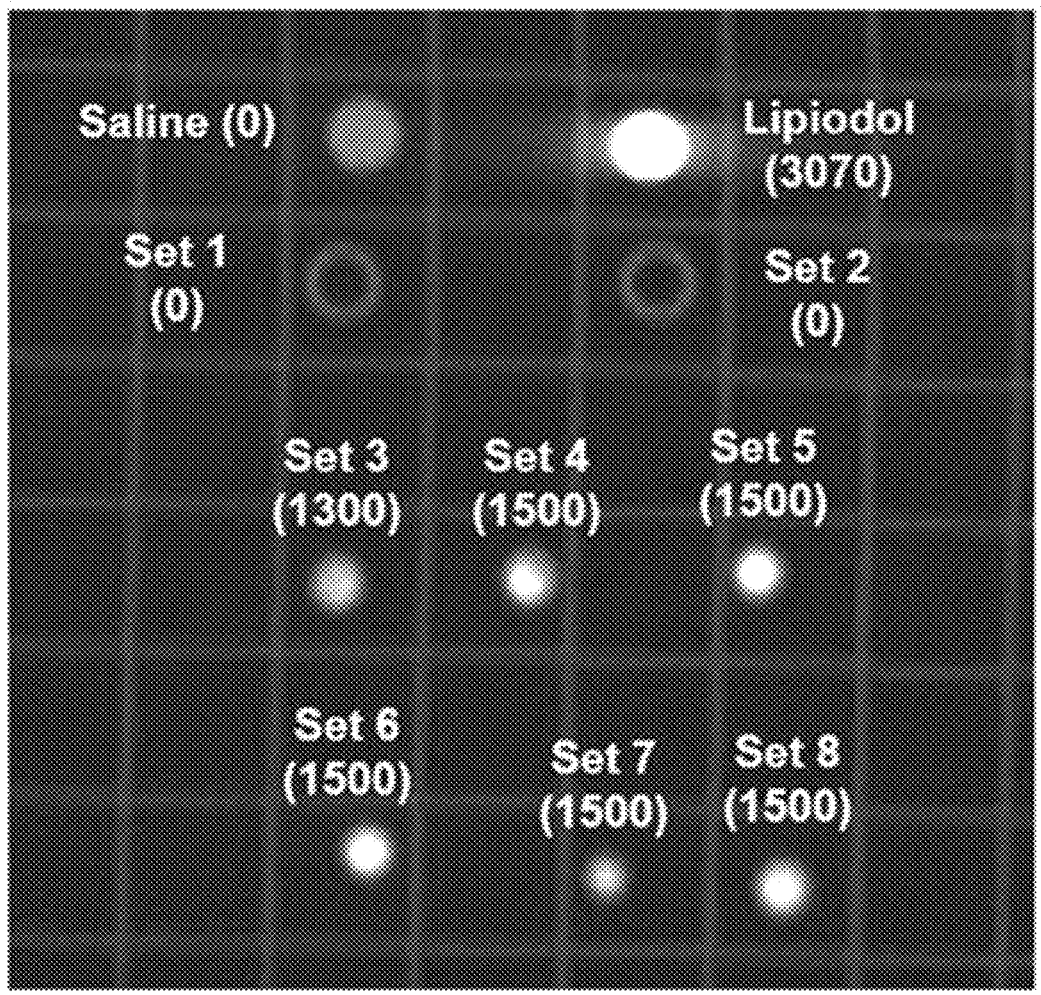
FIG. 11 shows the result of measuring the intensity of CT signals before and after composite synthesis while changing the mixing ratio of solvents.

Example 5. Measurement of In Vitro CT Signal of Composite of Present Invention 5-1. Evaluation of CT Signal Intensity In order to evaluate whether the composite of the present disclosure had sufficient CT intensity as a contrast agent, the CT signal intensities of Lipiodol, which is a conventional CT contrast agent, and the composite of the present disclosure were compared, and the results are shown in FIG. 11.

In Example 5-1, saline and Lipiodol which is a CT contrast agent were used as a negative control and a positive control, respectively. In addition, while using porous silicon microparticles (Set 1; synthesis starting material) as a comparative example, porous silicon microparticles oxidized using an aqueous borate solution (Set 2), particles of a composite of the present disclosure (Set 3), the above composite dispersed in distilled water (Set 4), the composite dispersed in a 1:3 mixture of distilled water and glycerol (Set 5), the composite dispersed in a 1:1 mixture of distilled water and glycerol (Set 6), the composite dispersed in a 3:1 mixture of distilled water and glycerol (Set 7), and the composite dispersed in pure glycerol (Set 8) were prepared as individual samples, and CT signal intensity was measured. According to the results, a CT signal of 1300 H.U. or more was measured only in Sets 3 to 8 including the composite of the present disclosure.

Through this, it was confirmed that the composite of the present disclosure had excellent properties as a CT contrast agent.

5-2. Confirmation of In Vivo Stability of Composite of Present Invention

The CT signal intensity of the composite of the present disclosure over time was analyzed in order to evaluate in vivo stability in the case of the decomposition of silver nanoparticles in the composite.

Figure 12:
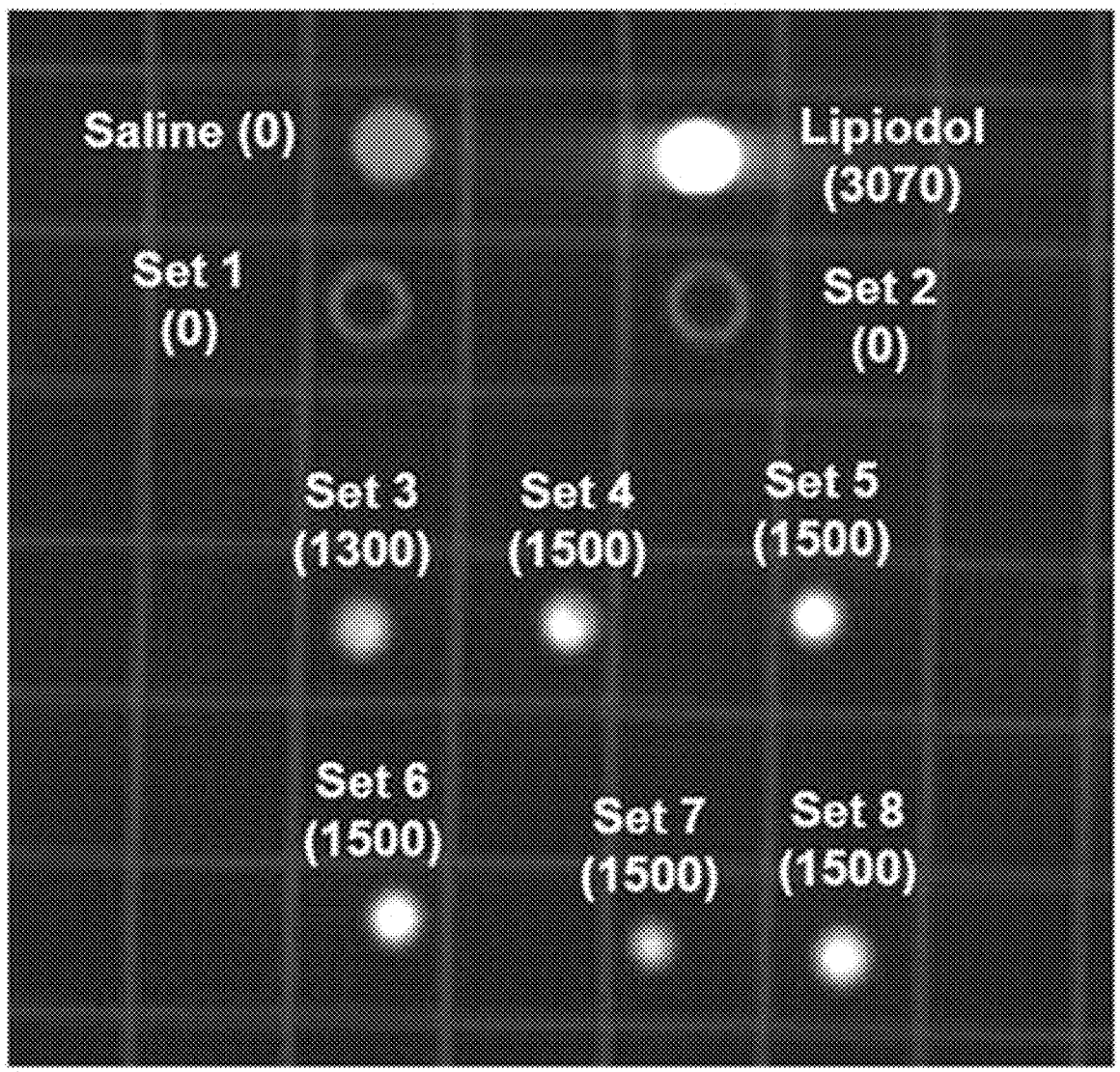
FIG. 12 shows the results of evaluating the success of injecting a mixture containing 75% glycerol by a syringe.
Figure 13:
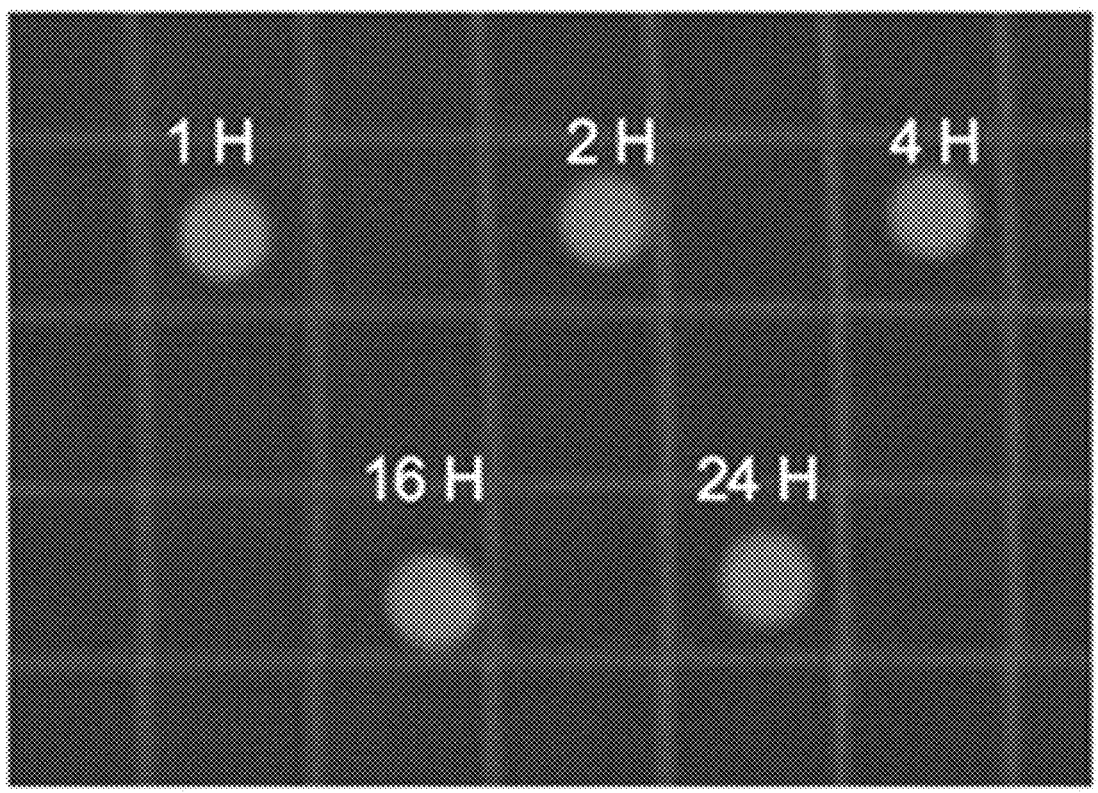
FIG. 13 shows the results of evaluating CT signal intensity after collecting the supernatant of a composite at various time points.
Figure 14:
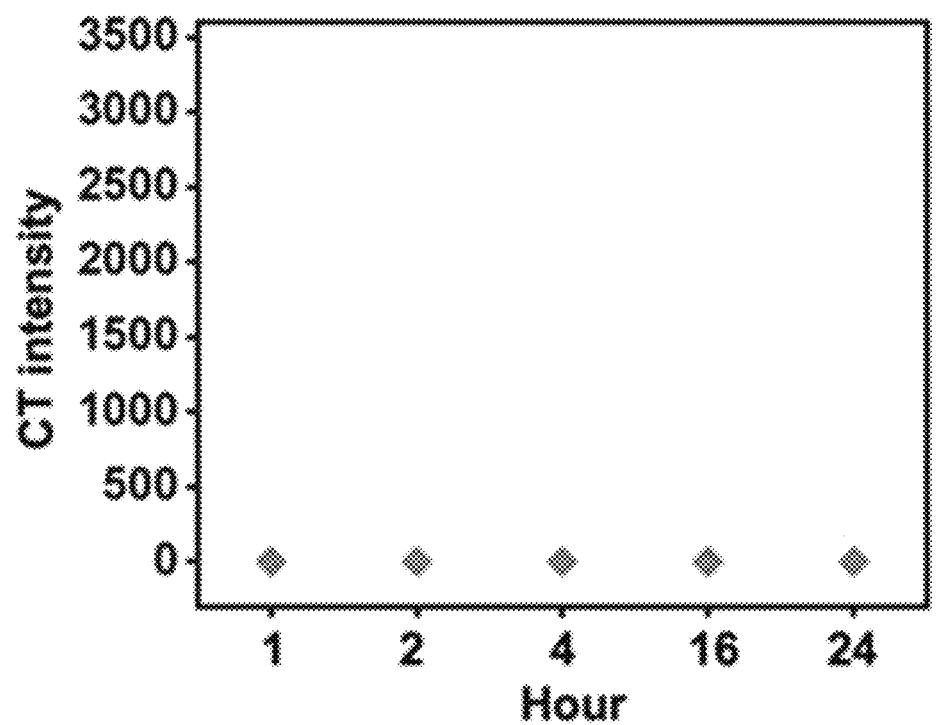
FIG. 14 is a graph showing the results of measuring CT signal intensity after collecting the supernatant of the composite of FIG. 13 at various time points.
Figure 15:
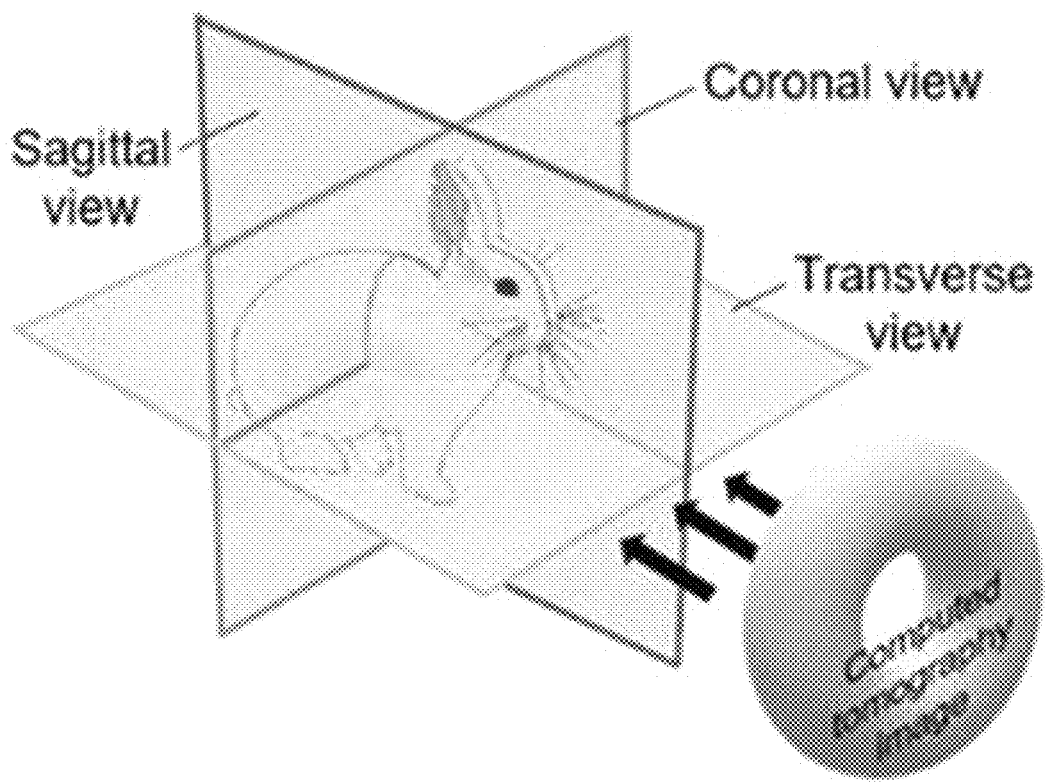
FIG. 15 is a schematic diagram for helping the understanding of the CT imaging of rabbits.

The optimal ratio of a glycerol solution mixed with the composite of the present disclosure was identified by injecting a diluted solution containing the composite into the rabbit's lungs by a localized targeted treatment specialist. As shown in FIG. 12, it was confirmed that when a water/glycerol mixture containing 75% glycerol (Set 5) was injected, the injection performed better. Subsequently, the CT signal intensity of the composite over time was analyzed through an in vitro analysis based on incubation performed for 24 hours at 37° C. As shown in FIGS. 13 and 14, it was confirmed that the decomposition-induced release of silver nanoparticles was not observed in the composition of the present disclosure.

Through this, it was confirmed that the composition of the present disclosure was not decomposed in vivo and maintained stability.

Figure 16:
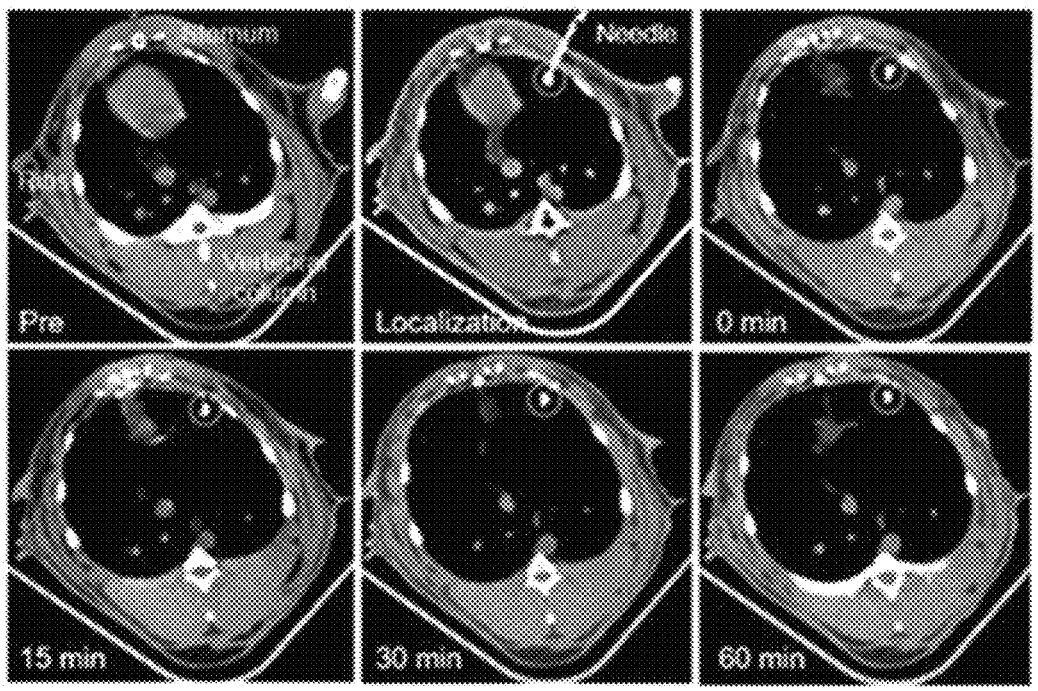
FIG. 16 shows in vivo lung CT images obtained from the chest of a rabbit using the composite.

Example 6. Confirmation of Possibility of In Vivo Localization Targeting Potential of Composite of Present Invention In order to confirm whether in vivo tissue localization target treatment potential of the composite of the present disclosure, rabbit lungs were treated with the composite, and targeting results were evaluated with in vivo CT imaging. As shown in FIG. 16, in micro-CT images of healthy rabbit chests, the lungs appeared dark, and the spine, sternum, and ribs appeared white. The composite of the present disclosure was injected into the lung tissue, and in vivo CT imaging was performed by real-time monitoring (yellow circle in a localized image; FIG. 16, upper center). The composite of the present disclosure was diluted in a 75% glycerol solution and injected into the lungs of rabbits, and then CT imaging was performed. The injected formulation was a form in which 20 mg of the composite according to the present disclosure was dispersed in 300 mL of a solvent including 75% glycerol and 25% water, and the entire amount of 300 mL was injected at one time. A high-contrast CT image was obtained at the site where the composite of the present disclosure was injected.

Figure 17:
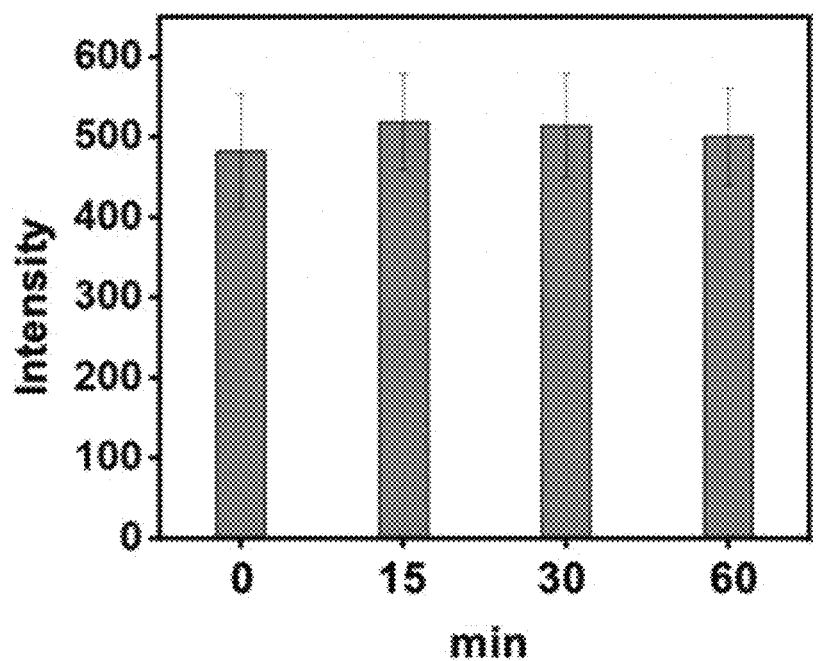
FIG. 17 is a graph showing the intensity of Hounsfield unit (HU) signals extracted from the above CT images.
Figure 18:
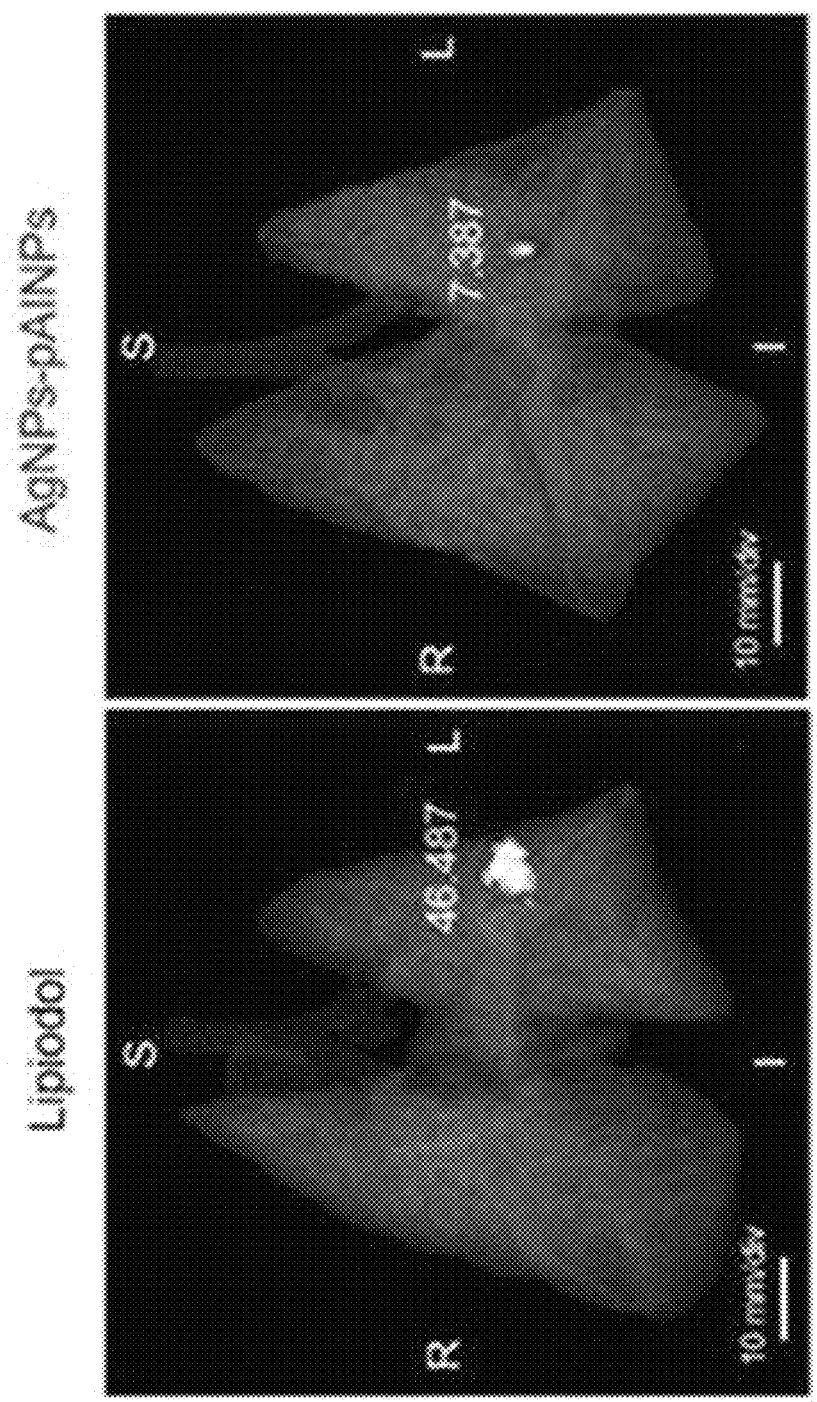
FIG. 18 shows in vivo CT images of rabbit lungs after injection of Lipiodol and the composite.

As shown in FIGS. 16 and 17, changes in diffusion rate and CT signal intensity were monitored for 60 minutes at the injection site, but no significant changes were observed. Subsequently, the diffusion rate of the injected composite of the present disclosure was compared with that of Lipiodol. As shown in FIG. 16, the same volumes (300 mL) of the composite of the present disclosure and Lipiodol were separately injected into the lungs of rabbits, and micro-CT images were analyzed within three minutes. While extensive CT area reactivity (46.487 $cm^2$ for two-dimensional (2D) area measurement) was monitored through three-dimensional (3D) CT imaging in the lungs of Lipiodol-treated rabbits, local area reactivity (7.387 $cm^2$) was observed in the lungs of rabbits treated with the composite of the present disclosure.

Through the above experiments, it was confirmed that the composite of the present disclosure can be sufficiently used for in vivo CT signal measurement and lung localization target processing for in vivo micro-CT imaging and as a new image-inducing localizing agent in CT imaging for lung cancer surgery.

Example 7. Evaluation of In Vivo Toxicity of Composite of Present Invention

In order to confirm the actual in vivo application potential of the composite of the present disclosure, an in vivo injection time and the occurrence of nephrotoxicity and immunotoxicity were evaluated. The in vivo toxicity of the composite of the present disclosure in mice (C57BL/6J, i.p. injection) was analyzed, and an LPS (10 mg/kg) was used as a positive control in the experiment.

Figure 19:
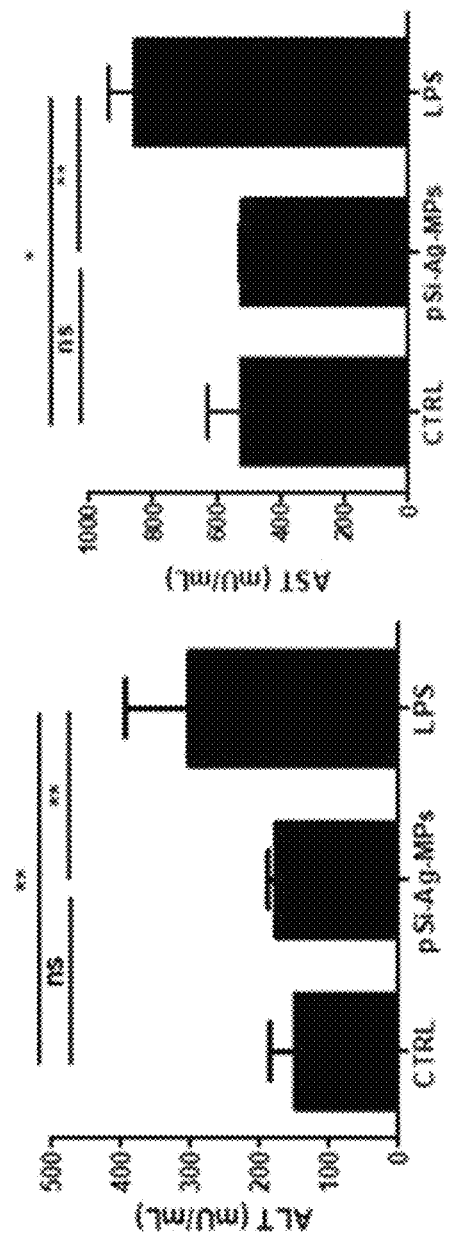
FIG. 19 shows the results of evaluating in vivo toxicity, which confirm that alanine transaminase (ALT) and aspartate transaminase (AST) levels are maintained in mouse serum after the injection of the composite.
Figure 20:
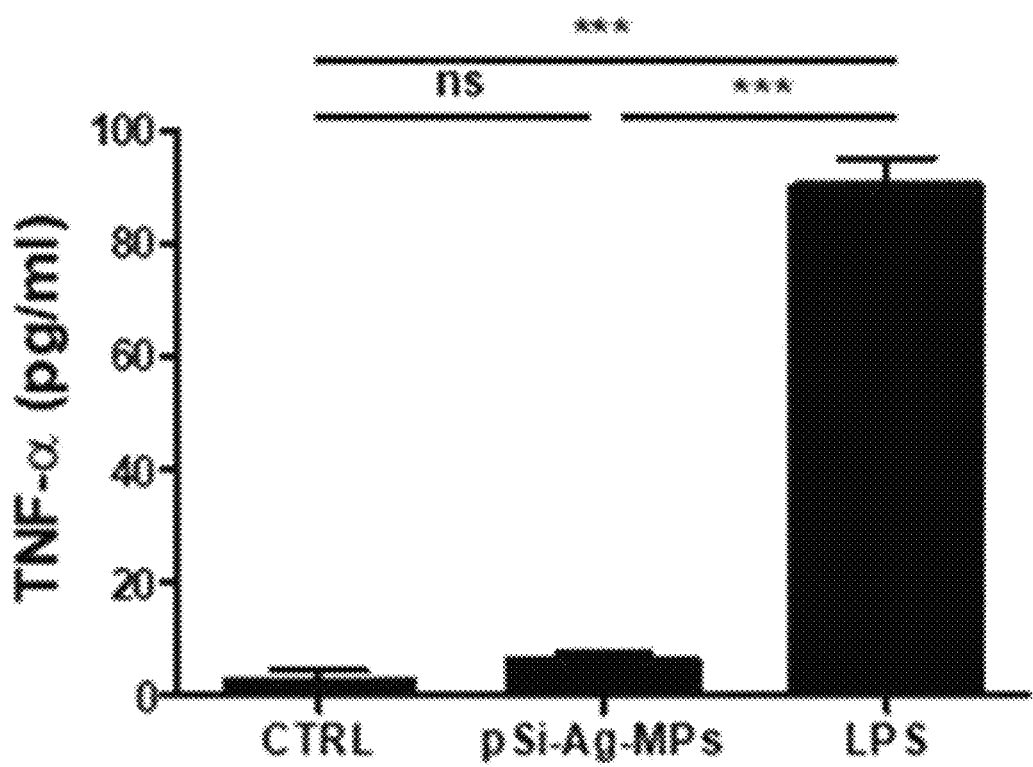
FIG. 20 shows the results of evaluating in vivo toxicity, which confirm that a tumor necrosis factor alpha (TNF-α) level is maintained in mouse serum after the injection of the composite.

As shown in FIG. 19, liver toxicity was not observed in a mouse group treated with the composite of the present disclosure. Also, as shown in FIG. 20, there was no significant change in the level of TNF-α, which is a major inflammatory cytokine, in the serum.

Figure 21:
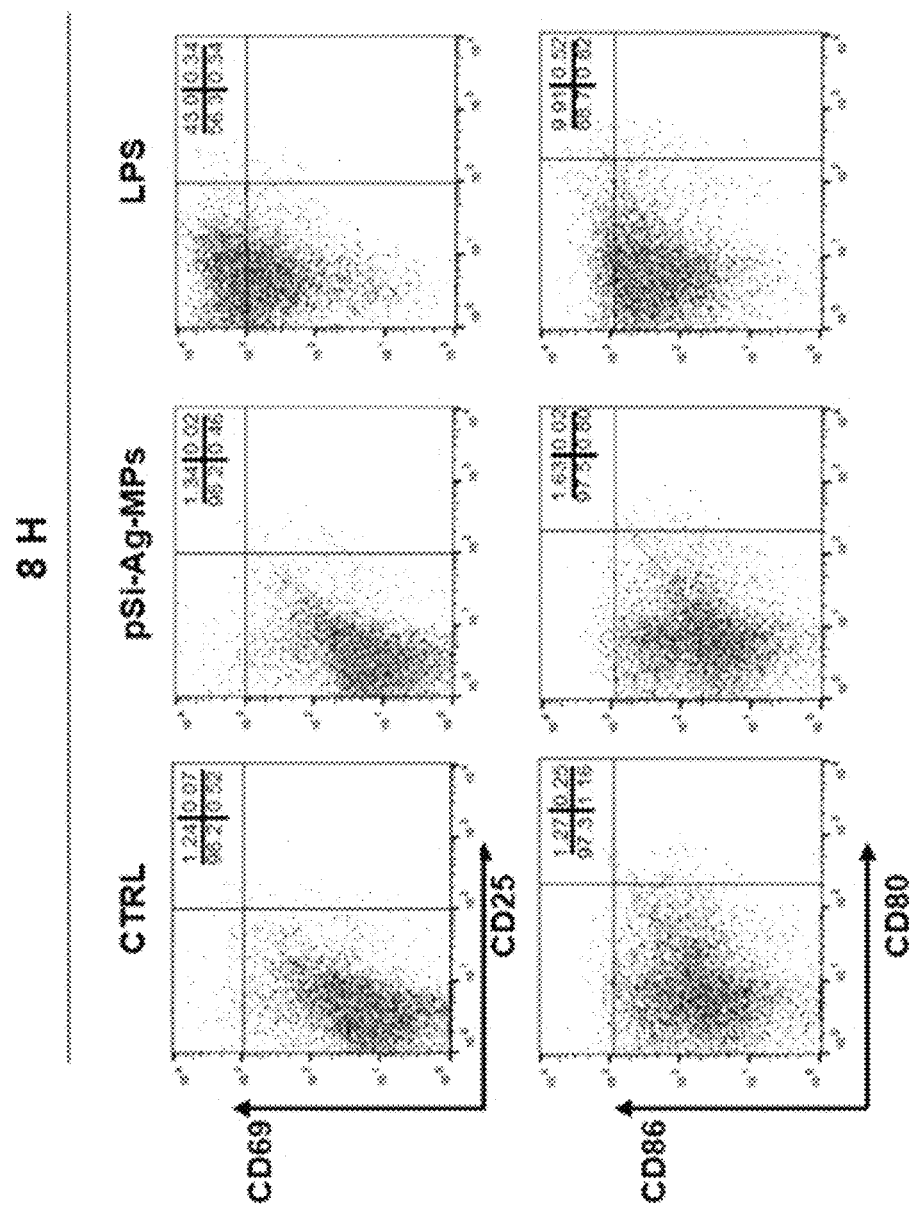
FIG. 21 shows results of confirming that there is no change in cell population activity at eight hours after the in vivo treatment of mice with the composite.
Figure 22:
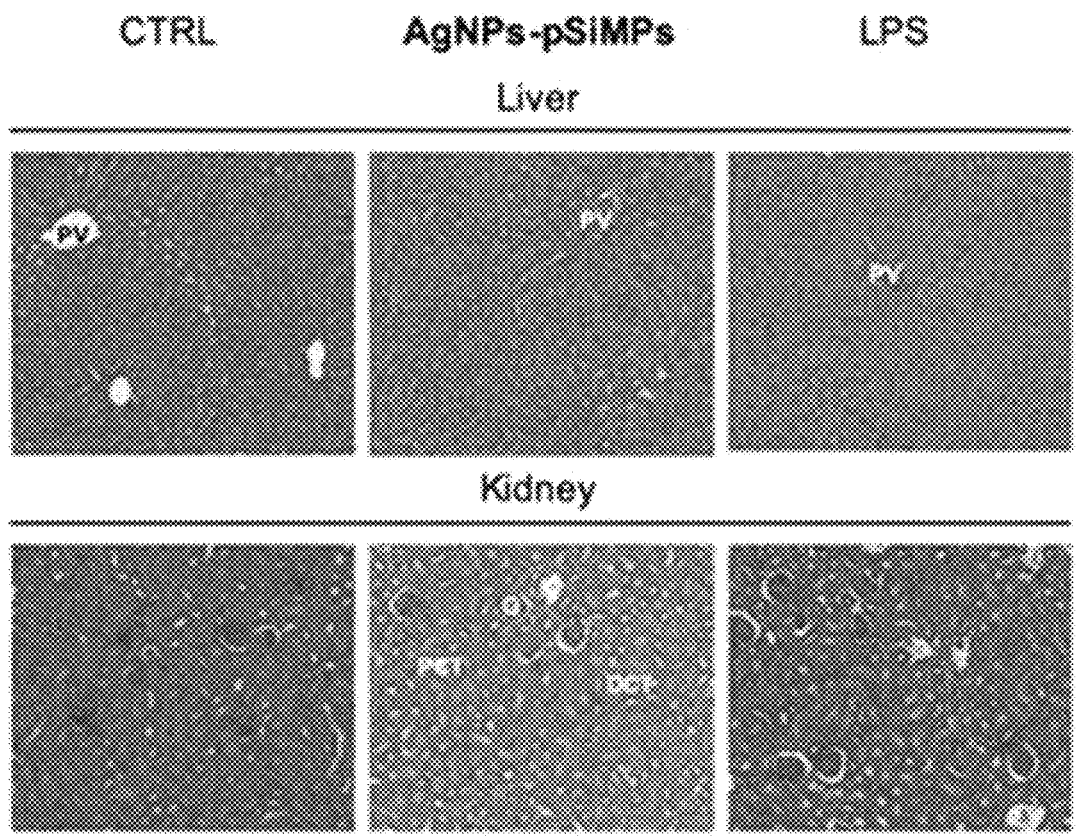
FIG. 22 shows results of confirming that there is no change in the liver and kidney tissues at eight hours after the in vivo treatment of mice with the composite.
Figure 23:
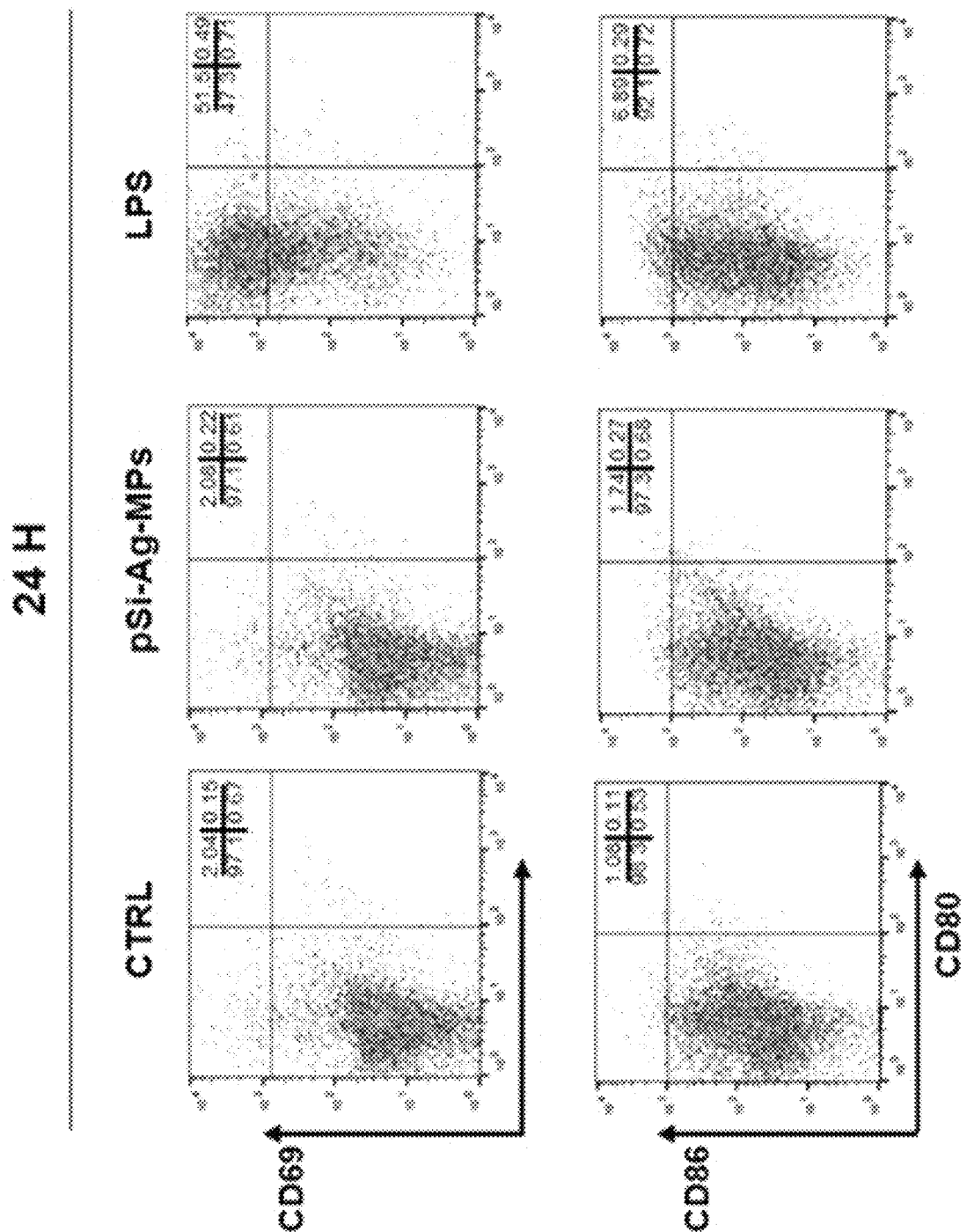
FIG. 23 shows results of confirming that there is no change in cell population activity at 24 hours after the in vivo treatment of mice with the composite.
Figure 24:
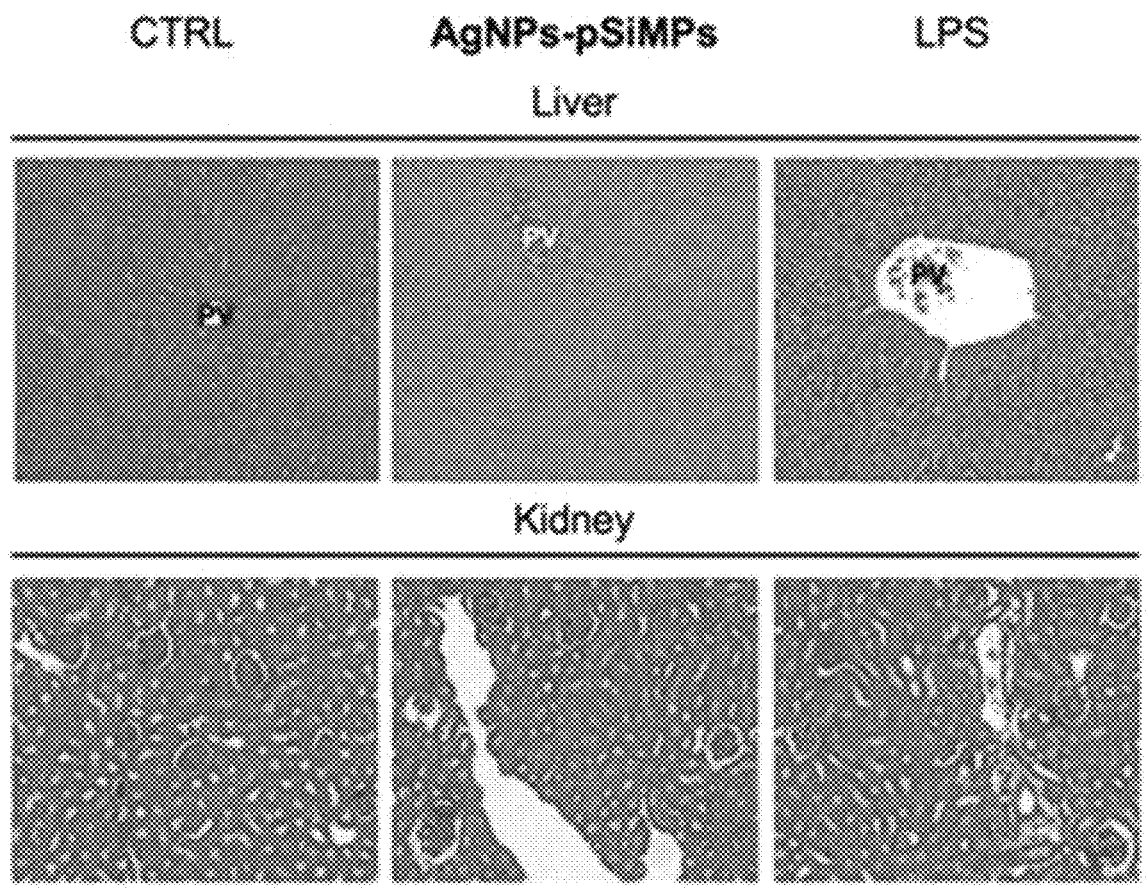
FIG. 24 shows results of confirming that there is no change in the liver and kidney tissues at 24 hours after the in vivo treatment of mice with the composite.
Figure 25:
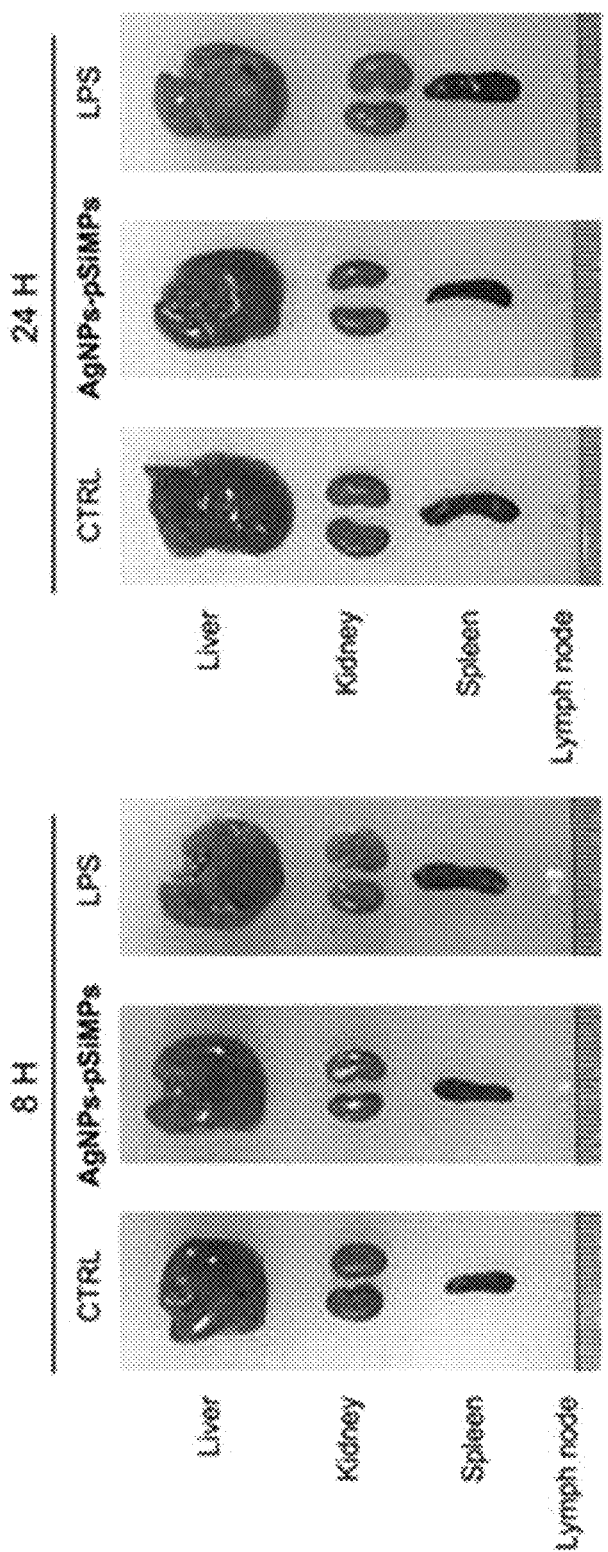
FIG. 25 shows results of confirming that there is no change in the size of the liver, kidney, and spleen at 8 and 24 hours after the in vivo treatment of mice with the composite.

The level of CD, which is one of the initial activation markers in T-cell activation, was analyzed in a double positive cell line (i.e., CD69+, CD25+), and as shown in FIG. 21, there was no significant activity of the cell population with respect to the composite of the present disclosure. Similarly, there were no significant changes in the expression levels of the co-stimulatory molecules CD80 and CD86, which are identified as active markers of dendritic cells, macrophages, and B-cells.

Also, as shown in FIGS. 22 to 25, no activated lymphocytes or histological changes were observed.

As such, the composite of the present disclosure does not affect the mouse immune system and shows almost no toxicity, confirming that it can be safely applied in the clinical field.

Since a biological tissue imaging agent of the present disclosure, which includes a composite of oxidized porous silicon microparticles and silver nanoparticles, continuously provides a stable image signal without spreading in the body as compared to conventional imaging agents, it is possible to increase surgical stability by accurately identifying target tissues in vivo in an affected area.

The above description of the present disclosure is for illustration, and those of ordinary skill in the art to which the present disclosure pertains will understand that the present disclosure can be easily modified into other specific forms without changing the technical spirit or essential characteristics thereof. Therefore, it should be understood that the exemplary embodiments described above are illustrative in all respects and not restrictive.

INDUSTRIAL APPLICABILITY

Since a biological tissue imaging composition of the present disclosure, which includes a composite of oxidized porous silicon microparticles and silver nanoparticles combined with the same, continuously provides an image signal without spreading in the body as compared to conventional imaging agents, it is possible to increase surgical stability by accurately identifying target tissues in vivo in an affected area.

What is claimed is:

1. A composition for imaging of biological tissue by computed tomography (CT), comprising a composite in which oxidized porous silicon microparticles and silver nanoparticles are combined,
    wherein the silver nanoparticles are bonded into pores of the oxidized porous silicon microparticles and attached to a surface of the oxidized porous silicon microparticles,
    wherein the composite is dissolved in a mixture of glycerol and water in a ratio of 3:1,
    wherein the composition has in vivo local area reactivity,
    wherein a size of the porous silicon microparticles is in a range of 1 μm to 10 μm, and
    wherein the composite includes elemental silicon, elemental oxygen, and elemental silver in a weight ratio of 100:100 to 120:15 to 30.

2. The composition of claim 1, wherein the biological tissue is lung tissue.

3. A method of manufacturing a composition for imaging of biological tissue by computed tomography (CT) according to claim 1, comprising steps of:
    a) oxidizing porous silicon microparticles;
    b) attaching silver nanoparticles to the oxidized silicon microparticles to create a composite; and
    c) dissolving the composite in a mixture of glycerol and water in a ratio of 3:1,
    wherein a size of the porous silicon microparticles is in a range of 1 μm to 10 μm, and
    wherein the composite includes elemental silicon, elemental oxygen, and elemental silver in a weight ratio of 100:100 to 120:15 to 30.

4. The method of claim 3, wherein the porous silicon microparticles oxidized in the step a) include an oxidized silicon (Si) framework ($SiO_2$).

5. The method of claim 3, wherein, in the step b), the attaching of the silver nanoparticles is achieved using an aqueous silver bis-amine solution ($[Ag(NH_3)_2]^+$).

6. The method of claim 3, wherein the oxidizing is achieved using a borate.

* * * * *